(12) United States Patent
Browse et al.

(10) Patent No.: US 10,351,871 B2
(45) Date of Patent: *Jul. 16, 2019

(54) DESATURASES AND METHODS OF USING THEM FOR SYNTHESIS OF POLYUNSATURATED FATTY ACIDS

(71) Applicant: Washington State University, Pullman, WA (US)

(72) Inventors: John A. Browse, Palouse, WA (US); James G. Wallis, Moscow, ID (US); Jennifer L. Watts, Moscow, ID (US)

(73) Assignee: Washington State University, Pullman, WA (US)

( * ) Notice: Subject to any disclaimer, the term of this patent is extended or adjusted under 35 U.S.C. 154(b) by 162 days.

This patent is subject to a terminal disclaimer.

(21) Appl. No.: 15/621,699

(22) Filed: Jun. 13, 2017

(65) Prior Publication Data

US 2017/0283839 A1      Oct. 5, 2017

Related U.S. Application Data

(60) Division of application No. 14/308,456, filed on Jun. 18, 2014, now Pat. No. 9,695,450, which is a division of application No. 13/406,248, filed on Feb. 27, 2012, now Pat. No. 8,791,327, which is a continuation of application No. 12/141,865, filed on Jun. 18, 2008, now Pat. No. 8,124,838, which is a division of application No. 10/975,692, filed on Oct. 26, 2004, now Pat. No. 7,402,735, which is a division of application No. 09/857,583, filed as application No. PCT/US99/28655 on Dec. 6, 1999, now Pat. No. 6,825,017.

(60) Provisional application No. 60/111,301, filed on Dec. 7, 1998.

(51) Int. Cl.
| | |
|---|---|
| *C12N 15/82* | (2006.01) |
| *C12N 15/80* | (2006.01) |
| *C12N 15/85* | (2006.01) |
| *C12N 9/02* | (2006.01) |

(52) U.S. Cl.
CPC ......... *C12N 15/8247* (2013.01); *C12N 15/80* (2013.01); *C12N 15/8241* (2013.01); *C12N 15/85* (2013.01); *C12N 9/0071* (2013.01); *C12N 9/0083* (2013.01)

(58) Field of Classification Search
None
See application file for complete search history.

(56) References Cited

U.S. PATENT DOCUMENTS

| | | | |
|---|---|---|---|
| 5,057,419 A | 10/1991 | Martin et al. | |
| 6,051,754 A | 4/2000 | Knutzon | |
| 6,051,755 A | 4/2000 | Zou et al. | |
| 6,825,017 B1 * | 11/2004 | Browse | C12N 9/0071 435/134 |
| 7,256,033 B2 | 8/2007 | Damude et al. | |
| 7,402,735 B2 * | 7/2008 | Browse | C12N 9/0071 800/298 |
| 8,124,838 B2 * | 2/2012 | Browse | C12N 9/0071 435/252.3 |
| 8,791,327 B2 * | 7/2014 | Browse | C12N 9/0083 800/281 |

FOREIGN PATENT DOCUMENTS

| | | |
|---|---|---|
| CA | 2315297 A1 | 7/1999 |
| WO | WO 96/21022 | 7/1996 |
| WO | WO 98/45461 | 10/1998 |
| WO | WO 98/46764 | 10/1998 |
| WO | WO 99/33958 | 7/1999 |
| WO | WO 2004/057001 | 7/2004 |

OTHER PUBLICATIONS

Beebe et al., "Elucidation of tRNA-dependent editing by a class II tRNA synthetase and significance for cell viability," *The EMBO Journal* 22(3): 668-675, 2003.
Bork et al., "Go hunting in sequence databases but watch out for the traps," *TIG*, 12(10): 425-427, 1996.
Brenner, "Errors in genome annotation," *TIG*, 15(4): 132-133, 1999.
Broun et al., "Catalytic Plasticity of Fatty Acid Modification Enzymes Underlying Chemical Diversity of Plant Lipids," *Science*, 282: 1315-1317, 1998.
Dock-Bregeon et al., "Transfer RNA-Mediated Editing in Threonyl-tRNA Synthetase: The Class II Solution to the Double Discrimination Problem," *Cell* 103:877-884, Dec. 8, 2000.
Doerks et al., "Protein annotation: detective work for function prediction," *TIG*, 14(6): 248-250, 1998.
Hirosawa et al., "Protein Multiple Sequence Alignment using Knowledge," *Proceedings of Hawaii International Conference on System Science*, 1:803-812, 1993.
Hulanicka et al., "Lipid Metabolism of *Euglena gracilis*," *The Journal of Biological Chemistry*, 239(9):2778-2787, Sep. 1964.
Lederer et al., "The cytochrome $b_5$-fold: An adaptable molecule," *Biochimie* 76:674-692, 1994.
Michaelson et al., "Functional identification of a fatty acid $\Delta^5$ desaturase gene from *Caenorhabditis elegans*," *FEBS Letters* 439:215-218, 1998.

(Continued)

*Primary Examiner* — Elizabeth F McElwain
(74) *Attorney, Agent, or Firm* — Klarquist Sparkman, LLP

(57) ABSTRACT

The amino acid and nucleic acid sequences of a $\Delta^5$-desaturase enzyme and a $\Delta^8$-desaturase enzyme are disclosed. The nucleic acid sequences can be used to design recombinant DNA constructs and vectors. These vectors can then be used to transform various organisms, including for example, plants and yeast. The transformed organisms will then produce polyunsaturated fatty acids. The amino acid sequences are useful for generating enzyme-specific antibodies that are useful for identifying the desaturases.

15 Claims, 21 Drawing Sheets

Specification includes a Sequence Listing.

(56) References Cited

OTHER PUBLICATIONS

Napier et al., "Identification of a *Caenorhabditis elegans* $\Delta^6$-fatty-acid-desaturase by heterologous expression in *Saccharomyces cerevisiae*," *Biochem. J.* 330:611-614, 1998.

Qi et al., "Production of very long chain polyunsaturated omega-e and omega-6 fatty acids in plants," *Nature Biotechnology* 22(6):739-745, Jun. 2004.

Sayanova et al., "Expression of a borage desaturase cDNA containing an N-terminal cytochrome $b_5$ domain results in the accumulation of high levels of $\Delta^6$-desaturated fatty acids in transgenic tobacco," *PNAS, USA* 94:4211-4216, Apr. 1997.

Sokabe et al., "Molecular basis of alanine discrimination in editing site," *PNAS*, 102(33):11669-11674, Aug. 16, 2005.

Spychalla et al., "Identification of an animal ω-3 fatty acid desaturase by heterologous expression in *Arabidopsis*," *PNAS, USA* 94:1142-1147, Feb. 1997.

Van de Loo et al., "An oleate 12-hydroxylase from *Ricinus communis* L. is a fatty acyl desaturase homolog," *PNAS, U.S.A.*, 92: 6743-6747, 1995.

Wallis et al., "The $\Delta^8$-Desaturase of *Euglena gracilis*: An Alternate Pathway for Synthesis of 20-Carbon Polyunsaturated Fatty Acids," *Archives of Biochemistry and Biophysics* 365(2):307-316, May 15, 1999.

\* cited by examiner

Δ-6 pathway
ω-3 fatty acids
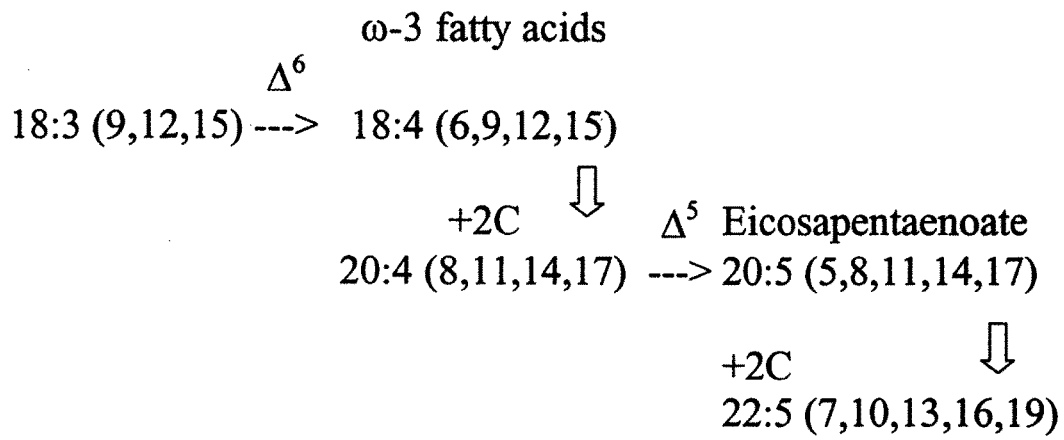
ω-6 fatty acids
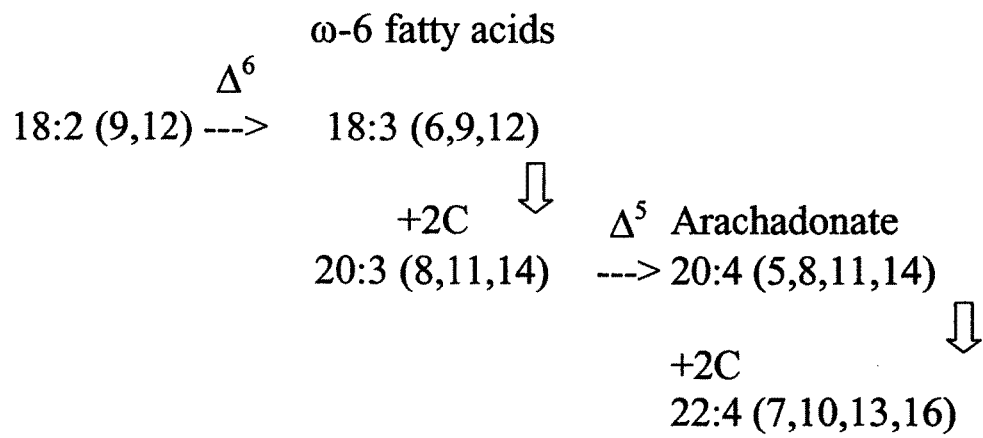
FIG. 1A

Δ-8 pathway
ω-3 fatty acids
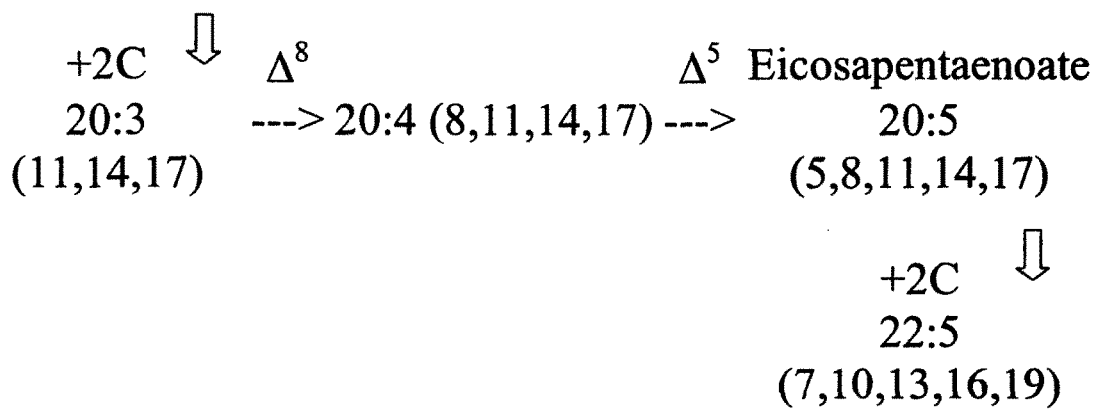
ω-fatty acids
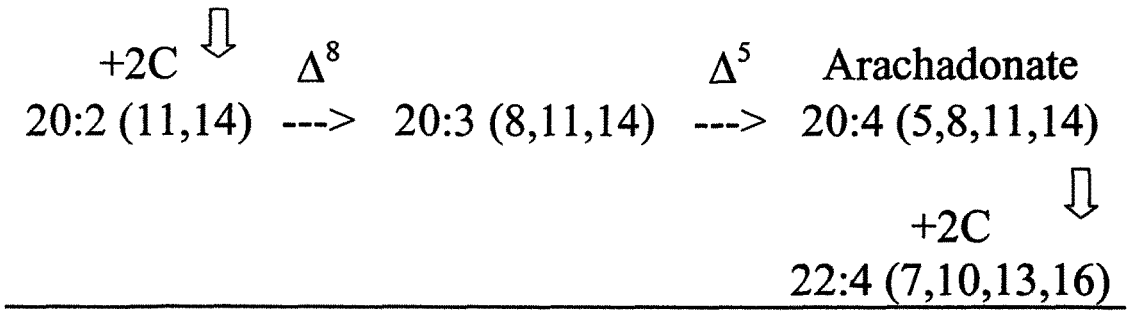
FIG. 1B

| PK | RT | FA | % | PK | RT | FA | |
|---|---|---|---|---|---|---|---|
| 1 | 10.0 | 20:2 Δ11,14 | 7.2 | 4 | 11.7 | 20:5 Δ5,8,11,14,17 | 6.2 |
| 2 | 10.3 | 20:3 Δ8,11,14 | 6.3 | 5 | 14.0 | 22:4 Δ7,10,13,16 | 2.9 |
| 3 | 10.7 | 20:4 Δ5,8,11,14 | 9.0 | 6 | 14.5 | 22:5 Δ4,7,10,13,16 | 1.8 |
| | 10.9 | 20:3 Δ11,14,17 | 1.4 | 7 | 15.2 | 22:5 Δ7,10,13,16,19 | 2.6 |
| | | | | 8 | 15.7 | 22:6 Δ4,7,10,13,16,19 | 2.0 |

```
fat-4    1  MVLREQEHEPFFIKIDGKWCQIDDAVLRSHPGGS.AITTYKNMDATTVFHTFHTGSKEAY
efd1     1  MKSKRQAL..PLTI..DGT.TYDVSAWVNFHPGGAEIIENYQGRDATDAFMVMH..SQEAF
fat-3    1  MVV.DKNASGLRMKVDGKWLYLSEELVKKHPGGA.VIEQYRNSDATHIFHAFHEGSSQAY
                     W              HPGG          G      F    H
                             Cytochrome b₅-like domain fat-4   60  QWLTELKKECPTQEPEIPDIKDDPIKGIDDVNMGTFNISEKRSAQINKSFTDLRMRVRAE
efd1    56  DKLKRMPK....................INPSSELPPQAAVNEAQEDFRKLREELIAT
fat-3   59  KQLDLLKKH..GEHDEFLEKQLEKRLDKVDINVSAYDVSVAQEKKMVESFEKLRQKLHDD fat-4  120  GLMDGSPLFYIRKILETIFTILFAFYLQ.YHTYYLPSAILMGVAWQQLGWLIHEFAHHQL
efd1    94  GMFDASPLWYSYKISTTLGLGVLGYFIMVQYQMYFIGAVLLGMEYQQMGWLSHDICHHQT
fat-3  117  GLMKANETYFLFKAISTLSIMAFAFYLQ.YLGWYITSACLLALAWQQFGWLTHEFCHQQP
                                                                HXXXHH fat-4  179  FKNRYYNDLASYFVGNFLQGFSSGGWKEQHNVHHAATNVVGRDGDLDLVPFYATVAEHLN
efd1   154  FKNRNWNNLVGLVFGNGLQGFSVTWWKDRHNAHHSATNVQGHDPDIDNLPLLAWSEDDVT
fat-3  176  TKNRPLNDTISLFFGNFLQGFSRDWWKDKHNTHHAATNVIDHDGDIDLAPLFAFIPGDLC
                                      HXXHH fat-4  239  NY..SQDSWVMTLFRWQHVHWTFMLPFLRLSWLLQSIIFVSQMPTHYYDYYRNTAIYEQV
efd1   214  RASPISRK....LIQFQQYYFLVICILLRFIWCFQSVLTVRSLKDRDNQFYRSQYKKEAI
fat-3   236 KYKASFEKAILKIVPYQHLYFTAMLPMLRFSWTGQSVQWVFKENQMEYKVYQRNAFWEQA fat-4  297  GLSLHWAW.SLGQLYFLPDWSTRIMFFLVSHLVGGFLLSHVVTFNHYSVEKFALSSNIMS
efd1   270  GLALHWTLKALFHLFFMPSIITSLLVFFVSELVGGFGIAIVVFMNHYPLEKIGDSVWDGH
fat-3  296  TIVGHWAW.VFYQLFLLPTWPLRVAYFIISQMGGGLLIAHVVTFNHNSVDKYPANSRILN fat-4  356  NYACLQIMTTRNMRPGRFIDWLWGGLNYQIEHHLFPTMPRHNLNTVMPLVKEFAAANGLP
efd1   330  GFSVGQIHETMNIRRGIITDWFFGGLNYQIEHHLWPTLPRHNLTAVSYQVEQICQKHNLP
fat-3  355  NFAALQILTTRNMTPSPFIDWLWGGLNYQIEHHLFPTMPRCNLNACMKYVKEWCKENNLP
                                                HXXHH fat-4  416  YMVDDYFTGFWLEIEQFRNIANVAAKITK.KIA
efd1   390  YRNPLPHEGLVILLRYLAVFARMAEKQPAGKAL
fat-3  415  YLVDDYFDGYAMNLQQLKNMAE...HIQA.KAA
```

FIG. 3

```
  1  MVLREQEHEP FFIKIDGKWC QIDDAVLRSH PGGSAITTYK NMDATTVFHT
 51  FHTGSKEAYQ WLTELKKECP TQEPEIPDIK DDPIKGIDDV NMGTFNISEK
101  RSAQINKSFT DLRMRVRAEG LMDGSPLFYI RKILETIFTI LFAFYLQYHT
151  YYLPSAILMG VAWQQLGWLI HEFAHHQLFK NRYYNDLASY FVGNFLQGFS
201  SGGWKEQHNV HHAATNVVGR DGDLDLVPFY ATVAEHLNNY SQDSWVMTLF
251  RWQHVHWTFM LPFLRLSWLL QSIIFVSQMP THYYDYYRNT AIYEQVGLSL
301  HWAWSLGQLY FLPDWSTKIM FFLVSHLVGG FLLSHVVTFN HYSVEKFALS
351  SNIMSNYACL QIMTTRNMRP GRFIDWLWGG LNYQIEHHLF PTMPRHNLNT
401  VMPLVKEFAA ANGLPYMVDD YFTGFWLEIE QFRNIANVAA KLTKKIA
```

FIG. 6A

```
   1  GAATTTTCAA TCCTCCTTGG GTCCCACCGC TGTGATATCA AAATGGTATT
  51  ACGAGAGCAA GAGCATGAGC CATTCTTCAT TAAAATTGAT GGAAAATGGT
 101  GTCAAATTGA CGATGCTGTC CTGAGATCAC ATCCAGGTGG TAGTGCAATT
 151  ACTACCTATA AAAATATGGA TGCCACTACC GTATTCCACA CATTCCATAC
 201  TGGTTCTAAA GAAGCGTATC AATGGCTGAC AGAATTGAAA AAAGAGTGCC
 251  CTACACAAGA ACCAGAGATC CCAGATATTA AGGATGACCC AATCAAAGGA
 301  ATTGATGATG TGAACATGGG AACTTTCAAT ATTTCTGAGA AACGATCTGC
 351  CCAAATAAAT AAAAGTTTCA CTGATCTACG TATGCGAGTT CGTGCAGAAG
 401  GACTTATGGA TGGATCTCCT TTGTTCTACA TTAGAAAAAT TCTTGAAACA
 451  AtCTTCACAA TTCTTTTTGC ATTCTACCTT CAATACCACA CATATTATCT
 501  TCCATCAGCT ATTCTAATGG GAGTTGCGTG GCAACAATTG GGATGGTTAA
 551  TCCATGAATT CGCACATCAT CAGTTGTTCA AAAACAGATA CTACAATGAT
 601  TTGGCCAGCT ATTTCGTTGG AAACTTTTTA CAAGGATTCT CATCTGGTGG
 651  TTGGAAAGAG CAGCACAATG TGCATCACGC AGCCACAAAT GTTGTTGGAC
 701  GAgACGGAGA TCTTGATTTA GTCCCATTCT ATGCTACAGT GGCAGAACAT
 751  CTCAACAATT ATTCTCAGGA TTCATGGGTT ATGACTCTAT TCAGATGGCA
 801  ACATGTTCAT TGGACATTCA TGTTACCATT CCTCCGTCTC TCGTGGCTTC
 851  TTCAGTCAAT CATTTTTGTT AGTCAGATGC CAACTCATTA TTATGACTAT
 901  TACAGAAATA CTGCGATTTA TGAACAGGTT GGTCTCTCTT TGCACTGGGC
 951  TTGGTCATTG GGTCaATTGT ATTTCCTACC CGATTGGTCA ACTAAAATAA
1001  TGTTCTTCCT TGTTTCTCAT CTTGTTGGAG GTTTCCTGCT CTCTCATGTA
1051  GTTACTTTCA ATCATTATTC AGTGGAGAAG TTTGCATTGA GCTCGAACAT
1101  CATGTCAAAT TACGCTTGTC TTCAAATCAT GACCACAAGA AATATGAGAC
1151  CTGGAAGATT CATTGACTGG CTTTGGGGAG GTCTTAACTA TCAGATTGAG
1201  CACCATCTTT TCCCAACGAT GCCACGACAC AACTTGAACA CTGTTATGCC
1251  ACTTGTTAAG GAGTTTGCAG CAGCAAATGG TTTACCATAC ATGGTCGACG
1301  ATTATTTCAC AGGATTCTGG CTTGAAATTG AGCAATTCCG AAATATTGCA
1351  AATGTTGCTG CTAAATTGAC TAAAAAGATT GCCTAGATTA CGATTAATTA
1401  ATCAATTTAT TTTCATGTTC TATTCGTGTG TTTTAATATT TTCCAAATTT
1451  TTACCTATTC C
```

FIG. 6B

```
  1  MKSKRQALSP  LQLMEQTYDV  SAWVNFHPGG  AEIIENYQGR  DATDAFMVMH
 51  FQEAFDKLKR  MPKINPSFEL  PPQAAVNEAQ  EDFRKLREEL  IATGMFDASP
101  LWYSYKISTT  LGLGVLGYFL  MVQYQMYFIG  AVLLGMHYQQ  MGWLSHDICH
151  HQTFKNRNWN  NLVGLVFGNG  LQGFSVTCWK  DRHNAHHSAT  NVQGHDPDID
201  NLPPLAWSED  DVTRASPISR  KLIQFQQYYF  LVICILLRFI  WCFQCVLTVR
251  SLKDRDNQFY  RSQYKKEAIG  LALHWTLKAL  FHLFFMPSIL  TSLLVFFVSE
301  LVGGFGIAIV  VFMNHYPLEK  IGDPVWDGHG  FSVGQIHETM  NIRRGIITDW
351  FFGGLNYQIE  HHLWPTLPRH  NLTAVSYQVE  QLCQKHNLPY  RNPLPHEGLV
401  ILLRYLAVFA  RMAEKQPAGK  AL
```

FIG. 7A

```
   1  ATTTTTTTTC GAAATGAAGT CAAAGCGCCA AGCGCTATCC CCCTTACAAT
  51  TGATGGAACA AACATATGAT GTGGTCAATT TCCACCCTGG TGGTGCGGAA
 101  ATTATAGAGA ATTACCAAGG AAGGGATGCC ACTGATGCCT TCATGGTTAT
 151  GCACTTTCAA GAAGCCTTCG ACAAGCTCAA GCGCATGCCC AAAATCAATC
 201  CCAGTTTTGA GTTGCCACCC CAGGCTGCAG TGAATGAAGC TCAAGAGGAT
 251  TTCCGGAAGC TCCGAGAAGA GTTGATCGCA ACTGGCATGT TTGATGCCTC
 301  CCCCCTCTGG TACTCATACA AAATCAGCAC CACACTGGGC CTTGGAGTGC
 351  TGGGTTATTT CCTGATGGTT CAGTATCAGA TGTATTTCAT TGGGGCAGTG
 401  TTGCTTGGGA TGCACTATCA ACAGATGGGC TGGCTTTCTC ATGACATTTG
 451  CCACCACCAG ACTTTCAAGA ACCGGAACTG GAACAACCTC GTGGGACTGG
 501  TATTTGGCAA TGGTCTGCAA GGTTTTTCCG TGACATGTTG GAAGGACAGA
 551  CACAATGCAC ATCATTCGGC AACCAATGTT CAAGGGCACG ACCCTGATAT
 601  TGACAACCTC CCCCCCTTAG CCTGGTCTGA GGATGACGTC ACACGGGCGT
 651  CACCGATTTC CCGCAAGCTC ATTCAGTTCC AGCAGTACTA TTTCTTGGTC
 701  ATCTGTATCT TGTTGCGGTT CATTTGGTGT TTCCAGTGCG TGTTGACCGT
 751  GCGCAGTTTG AAGGACAGAG ATAACCAATT CTATCGCTCT CAGTATAAGA
 801  AGGAGGCCAT TGGCCTCGCC CTGCACTGGA CCTTGAAGGC CCTGTTCCAC
 851  TTATTCTTTA TGCCCAGCAT CCTCACATCG CTGTTGGTGT TTTTCGTTTC
 901  GGAGCTGGTT GGCGGCTTCG GCATTGCGAT CGTGGTGTTC ATGAACCACT
 951  ACCCACTGGA GAAGATCGGG GACCCAGTCT GGGATGGCCA TGGATTCTCG
1001  GTTGGCCAGA TCCATGAGAC CATGAACATT CGGCGAGGGA TTATCACAGA
1051  TTGGTTTTTC GGAGGCTTGA ATTACCAGAT TGAGCACCAT TTGTGGCCGA
1101  CCCTCCCTCG CCACAACCTG ACAGCGGTTA GCTACCAGGT GGAACAGCTG
1151  TGCCAGAAGC ACAACCTGCC GTATCGGAAC CCGCTGCCCC ATGAAGGGTT
1201  GGTCATCCTG CTGCGCTATC TGGCGGTGTT CGCCCGGATG GCGGAGAAGC
1251  AACCCGCGGG GAAGGCTCTA TAAGG
```

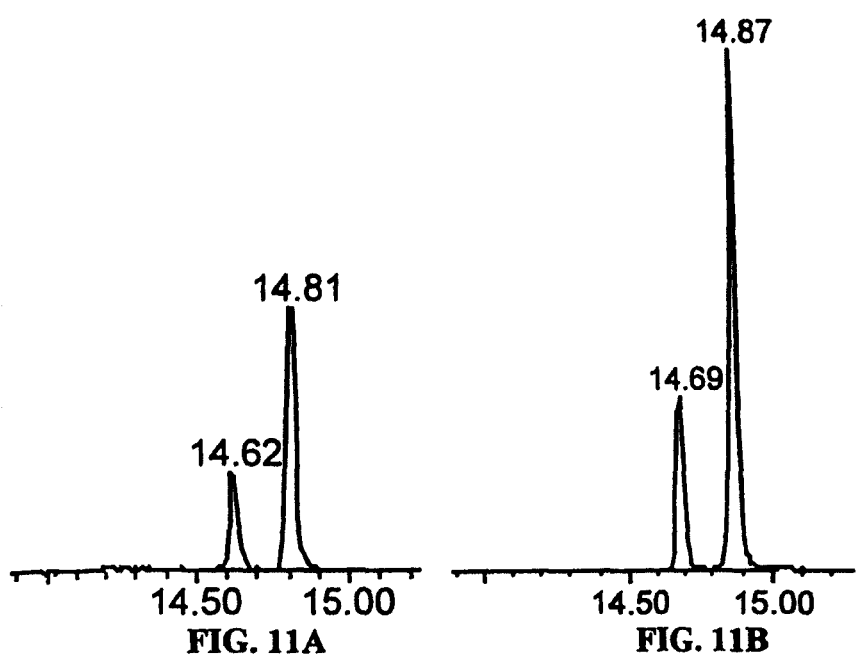

| FAT-3 (Δ6-desaturase) | | FAT-4 (Δ5-desaturase) | |
|---|---|---|---|
| substrate | % of substrate converted | substrate | % of substrate converted |
| 18:1Δ9 | 0 | 18:1Δ? | 5 |
| 18:2Δ9,12 | 14 | 18:2Δ9,12 | 0 |
| 18:3 Δ9,12,15 | 17 | 18:3 Δ9,12,15 | 0 |
| 20:1Δ11 | 0 | 20:1Δ11 | 0 |
| 20:2Δ11,14 | 0 | 20:2Δ11,14 | 27 |
| 20:3Δ11,14,17 | 0 | 20:3Δ11,14,17 | 26 |
| 20:3Δ8,11,14 | 0 | 20:3Δ8,11,14 | 55 |

FIG. 12

|  | pYES | | pYES-541 | |
|---|---|---|---|---|
|  | incorporation | desaturation | incorporation | desaturation |
| $\Delta^8$ Substrates | | | | |
| 20:3 (11,14,17) | 45.9 | 0 | 38.4 | 27.2 |
| 20:2 (11,14) | 16.7 | 0 | 21.3 | 14.8 |
| 20:1 (11) | 15.5 | 0 | 18.8 | 6.1 |
|  | | | | |
| $\Delta^6$ Substrates | | | | |
| 18:3 (9,12,15) | 20.9 | 0 | 19.2 | 0 |
| 18:2 (9,12) | 15.8 | 0 | 18.5 | 0 |
|  | | | | |
| $\Delta^5$ Substrates | | | | |
| 20:3 (8,11,14) | 34.4 | 0 | 35.6 | 0 |

FIG. 13

SEQUENCE LISTING

```
<160> NUMBER OF SEQ ID NOS: 17

<210> SEQ ID NO 1
<211> LENGTH: 1461
<212> TYPE: DNA
<213> ORGANISM: Caenorhabditis elegans

<400> SEQUENCE: 1
gaattttcaa tcctccttgg gtcccaccgc tgtgatatca aaatggtatt acgagagcaa      60
gagcatgagc cattcttcat taaaattgat ggaaaatggt gtcaaattga cgatgctgtc     120
ctgagatcac atccaggtgg tagtgcaatt actacctata aaaatatgga tgccactacc     180
gtattccaca cattccatac tggttctaaa gaagcgtatc aatggctgac agaattgaaa     240
aaagagtgcc ctacacaaga accagagatc ccagatatta aggatgaccc aatcaaagga     300
attgatgatg tgaacatggg aactttcaat atttctgaga aacgatctgc ccaaataaat     360
aaaagtttca ctgatctacg tatgcgagtt cgtgcagaag gacttatgga tggatctcct     420
```

-continued

```
ttgttctaca ttagaaaaat tcttgaaaca atcttcacaa ttcttttgc attctacctt      480 caataccaca catattatct tccatcagct attctaatgg agttgcgtg gcaacaattg       540 ggatggttaa tccatgaatt cgcacatcat cagttgttca aaaacagata ctacaatgat     600
ttggccagct atttcgttgg aaactttta caaggattct catctggtgg ttggaaagag      660
cagcacaatg tgcatcacgc agccacaaat gttgttggac gagacggaga tcttgattta    720
gtcccattct atgctacagt ggcagaacat ctcaacaatt attctcagga ttcatgggtt    780
atgactctat tcagatggca acatgttcat tggacattca tgttaccatt cctccgtctc    840
tcgtggcttc ttcagtcaat catttttgtt agtcagatgc caactcatta ttatgactat    900
tacagaaata ctgcgattta tgaacaggtt ggtctctctt tgcactgggc ttggtcattg    960
ggtcaattgt atttcctacc cgattggtca actagaataa tgttcttcct tgtttctcat   1020
cttgttggag gtttcctgct ctctcatgta gttactttca atcattattc agtggagaag   1080
tttgcattga gctcgaacat catgtcaaat tacgcttgtc ttcaaatcat gaccacaaga   1140
aatatgagac ctggaagatt cattgactgg ctttggggag tcttaactac tcagattgag    1200
caccatcttt tcccaacgat gccacgacac aacttgaaca ctgttatgcc acttgttaag   1260
gagtttgcag cagcaaatgg tttaccatac atggtcgacg attatttcac aggattctgg   1320
cttgaaattg agcaattccg aaatattgca atgttgctg ctaaattgac taaaaagatt    1380
gcctagatta cgattaatta atcaatttat tttcatgttc tattcgtgtg ttttaatatt   1440
ttccaaattt ttacctattc c                                              1461
```

<210> SEQ ID NO 2
<211> LENGTH: 447
<212> TYPE: PRT
<213> ORGANISM: Caenorhabditis elegans

<400> SEQUENCE: 2

```
Met Val Leu Arg Glu Gln Glu His Glu Pro Phe Phe Ile Lys Ile Asp
1               5                   10                  15

Gly Lys Trp Cys Gln Ile Asp Asp Ala Val Leu Arg Ser His Pro Gly
            20                  25                  30

Gly Ser Ala Ile Thr Thr Tyr Lys Asn Met Asp Ala Thr Val Phe
        35                  40                  45

His Thr Phe His Thr Gly Ser Lys Glu Ala Tyr Gln Trp Leu Thr Glu
    50                  55                  60

Leu Lys Lys Glu Cys Pro Thr Gln Glu Pro Glu Ile Pro Asp Ile Lys
65                  70                  75                  80

Asp Asp Pro Ile Lys Gly Ile Asp Asp Val Asn Met Gly Thr Phe Asn
                85                  90                  95

Ile Ser Glu Lys Arg Ser Ala Gln Ile Asn Lys Ser Phe Thr Asp Leu
            100                 105                 110

Arg Met Arg Val Arg Ala Glu Gly Leu Met Asp Gly Ser Pro Leu Phe
        115                 120                 125

Tyr Ile Arg Lys Ile Leu Glu Thr Ile Phe Thr Ile Leu Phe Ala Phe
    130                 135                 140

Tyr Leu Gln Tyr His Thr Tyr Tyr Leu Pro Ser Ala Ile Leu Met Gly
145                 150                 155                 160

Val Ala Trp Gln Gln Leu Gly Trp Leu Ile His Glu Phe Ala His His
                165                 170                 175

Gln Leu Phe Lys Asn Arg Tyr Tyr Asn Asp Leu Ala Ser Tyr Phe Val
            180                 185                 190
```

Gly Asn Phe Leu Gln Gly Phe Ser Ser Gly Gly Trp Lys Glu Gln His
        195                 200                 205

Asn Val His His Ala Ala Thr Asn Val Val Gly Arg Asp Gly Asp Leu
    210                 215                 220

Asp Leu Val Pro Phe Tyr Ala Thr Val Ala Glu His Leu Asn Asn Tyr
225                 230                 235                 240

Ser Gln Asp Ser Trp Val Met Thr Leu Phe Arg Trp Gln His Val His
                245                 250                 255

Trp Thr Phe Met Leu Pro Phe Leu Arg Leu Ser Trp Leu Leu Gln Ser
            260                 265                 270

Ile Ile Phe Val Ser Gln Met Pro Thr His Tyr Tyr Asp Tyr Tyr Arg
        275                 280                 285

Asn Thr Ala Ile Tyr Glu Gln Val Gly Leu Ser Leu His Trp Ala Trp
    290                 295                 300

Ser Leu Gly Gln Leu Tyr Phe Leu Pro Asp Trp Ser Thr Arg Ile Met
305                 310                 315                 320

Phe Phe Leu Val Ser His Leu Val Gly Gly Phe Leu Ser His Val
                325                 330                 335

Val Thr Phe Asn His Tyr Ser Val Glu Lys Phe Ala Leu Ser Ser Asn
            340                 345                 350

Ile Met Ser Asn Tyr Ala Cys Leu Gln Ile Met Thr Thr Arg Asn Met
        355                 360                 365

Arg Pro Gly Arg Phe Ile Asp Trp Leu Trp Gly Leu Asn Tyr Gln
    370                 375                 380

Ile Glu His His Leu Phe Pro Thr Met Pro Arg His Asn Leu Asn Thr
385                 390                 395                 400

Val Met Pro Leu Val Lys Glu Phe Ala Ala Asn Gly Leu Pro Tyr
                405                 410                 415

Met Val Asp Asp Tyr Phe Thr Gly Phe Trp Leu Glu Ile Glu Gln Phe
            420                 425                 430

Arg Asn Ile Ala Asn Val Ala Ala Lys Leu Thr Lys Lys Ile Ala
    435                 440                 445

<210> SEQ ID NO 3
<211> LENGTH: 1281
<212> TYPE: DNA
<213> ORGANISM: Euglena gracilis

<400> SEQUENCE: 3

```
atttttttc gaaatgaagt caaagcgcca agcgcttccc cttacaattg atggaacaac    60
atatgatgtg tctgcctggg tcaatttcca ccctggtggt gcggaaatta tagagaatta   120
ccaaggaagg gatgccactg atgccttcat ggttatgcac tctcaagaag ccttcgacaa   180
gctcaagcgc atgcccaaaa tcaatcccag ttctgagttg ccaccccagg ctgcagtgaa   240
tgaagctcaa gaggatttcc ggaagctccg agaagagttg atcgcaactg gcatgtttga   300
tgcctccccc ctctggtact catacaaaat cagcaccaca ctgggccttg gagtgctggg   360
ttatttcctg atggttcagt atcagatgta tttcattggg gcagtgttgc ttgggatgca   420
ctatcaacag atgggctggc tttctcatga catttgccac caccagactt tcaagaaccg   480
gaactggaac aacctcgtgg actggtatt tggcaatggt ctgcaaggtt tttccgtgac   540
atggtggaag gacagacaca atgcacatca ttcggcaacc aatgttcaag ggacgaccc   600 tgatattgac aacctccccc tcttagcctg gtctgaggat gacgtcacac gggcgtcacc   660
```

-continued

```
gatttcccgc aagctcattc agttccagca gtattatttc ttggtcatct gtatcttgtt      720
gcggttcatt tggtgtttcc agagcgtgtt gaccgtgcgc agtctgaagg acagagataa      780
ccaattctat cgctctcagt ataagaagga ggccattggc ctcgccctgc attggacatt      840
gaaggccctg ttccacttat tctttatgcc cagcatcctc acatcgctgt tggtattttt      900
cgtttcggag ctggttggcg gcttcggcat tgcgatcgtg gtgttcatga accactaccc      960
actggagaag atcggggact cggtctggga tggccatgga ttctcggttg ccagatccat     1020
tgagaccatg aacattcggc gagggattat cacagattgg ttttcggag cttgaacta      1080 ccagatcgag caccatttgt ggccgaccct ccctcgccac aacctgacag cggttagcta     1140
ccaggtggaa cagctgtgcc agaagcacaa cctgccgtat cggaacccgc tgccccatga     1200
agggttggtc atcctgctgc gctatctggc ggtgttcgcc cggatggcgg agaagcaacc     1260
cgccgggaag gctctataag g                                               1281
```

<210> SEQ ID NO 4
<211> LENGTH: 421
<212> TYPE: PRT
<213> ORGANISM: Euglena gracilis

<400> SEQUENCE: 4

```
Met Lys Ser Lys Arg Gln Ala Leu Pro Leu Thr Ile Asp Gly Thr Thr
 1               5                  10                  15

Tyr Asp Val Ser Ala Trp Val Asn Phe His Pro Gly Gly Ala Glu Ile
             20                  25                  30

Ile Glu Asn Tyr Gln Gly Arg Asp Ala Thr Asp Ala Phe Met Val Met
         35                  40                  45

His Ser Gln Glu Ala Phe Asp Lys Leu Lys Arg Met Pro Lys Ile Asn
     50                  55                  60

Pro Ser Ser Glu Leu Pro Pro Gln Ala Ala Val Asn Glu Ala Gln Glu
 65                  70                  75                  80

Asp Phe Arg Lys Leu Arg Glu Glu Leu Ile Ala Thr Gly Met Phe Asp
                 85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
    130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
    210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
```

-continued

```
                260                 265                 270
His Trp Thr Leu Lys Ala Leu Phe His Leu Phe Phe Met Pro Ser Ile
                275                 280                 285

Leu Thr Ser Leu Leu Val Phe Phe Val Ser Glu Leu Val Gly Gly Phe
            290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
            355                 360                 365

His Asn Leu Thr Ala Val Ser Tyr Gln Val Glu Gln Leu Cys Gln Lys
            370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420

<210> SEQ ID NO 5
<211> LENGTH: 27
<212> TYPE: DNA
<213> ORGANISM: artificial sequence
<220> FEATURE:
<223> OTHER INFORMATION: PCR Primer
<220> FEATURE:
<221> NAME/KEY: misc_feature
<222> LOCATION: (12)..(12)
<223> OTHER INFORMATION: n = a, t, g, or c

<400> SEQUENCE: 5
ggctggctga cncaygartt ytgycay                                    27

<210> SEQ ID NO 6
<211> LENGTH: 30
<212> TYPE: DNA
<213> ORGANISM: artificial sequence
<220> FEATURE:
<223> OTHER INFORMATION: PCR Primer
<220> FEATURE:
<221> NAME/KEY: misc_feature
<222> LOCATION: (13)..(13)
<223> OTHER INFORMATION: n = a, t, g, or c

<400> SEQUENCE: 6
catcgttgga aanarrtgrt gytcdatytg                                 30

<210> SEQ ID NO 7
<211> LENGTH: 41
<212> TYPE: DNA
<213> ORGANISM: artificial sequence
<220> FEATURE:
<223> OTHER INFORMATION: PCR Primer

<400> SEQUENCE: 7
cccgggaagc ttctcgagga attttcaatc ctccttgggt c                    41

<210> SEQ ID NO 8
<211> LENGTH: 34
```

```
<212> TYPE: DNA
<213> ORGANISM: artificial sequence
<220> FEATURE:
<223> OTHER INFORMATION: PCR Primer

<400> SEQUENCE: 8
cccgggtgga tccggaacat atcacacgaa acag                                34

<210> SEQ ID NO 9
<211> LENGTH: 6
<212> TYPE: RNA
<213> ORGANISM: artificial sequence
<220> FEATURE:
<223> OTHER INFORMATION: Consensus sequence
<220> FEATURE:
<221> NAME/KEY: polyA_signal
<222> LOCATION: (1)..(6)

<400> SEQUENCE: 9 aauaaa                                                                6

<210> SEQ ID NO 10
<211> LENGTH: 20
<212> TYPE: DNA
<213> ORGANISM: artificial sequence
<220> FEATURE:
<223> OTHER INFORMATION: PCR Primer

<400> SEQUENCE: 10
tctgggatct ctggttcttg                                                20

<210> SEQ ID NO 11
<211> LENGTH: 9
<212> TYPE: RNA
<213> ORGANISM: artificial sequence
<220> FEATURE:
<223> OTHER INFORMATION: Consensus sequence
<220> FEATURE:
<221> NAME/KEY: misc_feature
<222> LOCATION: (1)..(9)
<223> OTHER INFORMATION: Histidine box

<400> SEQUENCE: 11 uuuuuuucg                                                             9

<210> SEQ ID NO 12
<211> LENGTH: 5
<212> TYPE: PRT
<213> ORGANISM: artificial sequence
<220> FEATURE:
<223> OTHER INFORMATION: Consensus sequence
<220> FEATURE:
<221> NAME/KEY: MISC_FEATURE
<222> LOCATION: (1)..(5)
<223> OTHER INFORMATION: Histidine box
<220> FEATURE:
<221> NAME/KEY: MISC_FEATURE
<222> LOCATION: (2)..(3)
<223> OTHER INFORMATION: Xaa = any amino acid

<400> SEQUENCE: 12

His Xaa Xaa His His
 1               5

<210> SEQ ID NO 13
<211> LENGTH: 5
<212> TYPE: PRT
<213> ORGANISM: artificial sequence
<220> FEATURE:
```

```
<223> OTHER INFORMATION: Consensus sequence
<220> FEATURE:
<221> NAME/KEY: MISC_FEATURE
<222> LOCATION: (1)..(5)
<223> OTHER INFORMATION: Histidine box
<220> FEATURE:
<221> NAME/KEY: MISC_FEATURE
<222> LOCATION: (2)..(3)
<223> OTHER INFORMATION: Xaa = any amino acid

<400> SEQUENCE: 13

Gln Xaa Xaa His His
1               5

<210> SEQ ID NO 14
<211> LENGTH: 443
<212> TYPE: PRT
<213> ORGANISM: Caenorhabditis elegans

<400> SEQUENCE: 14

Met Val Val Asp Lys Asn Ala Ser Gly Leu Arg Met Lys Val Asp Gly
1               5                   10                  15

Lys Trp Leu Tyr Leu Ser Glu Glu Leu Val Lys Lys His Pro Gly Gly
            20                  25                  30

Ala Val Ile Glu Gln Tyr Arg Asn Ser Asp Ala Thr His Ile Phe His
        35                  40                  45

Ala Phe His Glu Gly Ser Ser Gln Ala Tyr Lys Gln Leu Asp Leu Leu
    50                  55                  60

Lys Lys His Gly Glu His Asp Glu Phe Leu Glu Lys Gln Leu Glu Lys
65                  70                  75                  80

Arg Leu Asp Lys Val Asp Ile Asn Val Ser Ala Tyr Asp Val Ser Val
                85                  90                  95

Ala Gln Glu Lys Lys Met Val Glu Ser Phe Glu Lys Leu Arg Gln Lys
            100                 105                 110

Leu His Asp Asp Gly Leu Met Lys Ala Asn Glu Thr Tyr Phe Leu Phe
        115                 120                 125

Lys Ala Ile Ser Thr Leu Ser Ile Met Ala Phe Ala Phe Tyr Leu Gln
    130                 135                 140

Tyr Leu Gly Trp Tyr Ile Thr Ser Ala Cys Leu Leu Ala Leu Ala Trp
145                 150                 155                 160

Gln Gln Phe Gly Trp Leu Thr His Glu Phe Cys His Gln Gln Pro Thr
                165                 170                 175

Lys Asn Arg Pro Leu Asn Asp Thr Ile Ser Leu Phe Phe Gly Asn Phe
            180                 185                 190

Leu Gln Gly Phe Ser Arg Asp Trp Trp Lys Asp Lys His Asn Thr His
        195                 200                 205

His Ala Ala Thr Asn Val Ile Asp His Asp Gly Asp Ile Asp Leu Ala
    210                 215                 220

Pro Leu Phe Ala Phe Ile Pro Gly Asp Leu Cys Lys Tyr Lys Ala Ser
225                 230                 235                 240

Phe Glu Lys Ala Ile Leu Lys Ile Val Pro Tyr Gln His Leu Tyr Phe
                245                 250                 255

Thr Ala Met Leu Pro Met Leu Arg Phe Ser Trp Thr Gly Gln Ser Val
            260                 265                 270

Gln Trp Val Phe Lys Glu Asn Gln Met Glu Tyr Lys Val Tyr Gln Arg
        275                 280                 285

Asn Ala Phe Trp Glu Gln Ala Thr Ile Val Gly His Trp Ala Trp Val
    290                 295                 300
```

```
Phe Tyr Gln Leu Phe Leu Leu Pro Thr Trp Pro Leu Arg Val Ala Tyr
305                 310                 315                 320

Phe Ile Ile Ser Gln Met Gly Gly Gly Leu Leu Ile Ala His Val Val
            325                 330                 335

Thr Phe Asn His Asn Ser Val Asp Lys Tyr Pro Ala Asn Ser Arg Ile
        340                 345                 350

Leu Asn Asn Phe Ala Ala Leu Gln Ile Leu Thr Thr Arg Asn Met Thr
    355                 360                 365

Pro Ser Pro Phe Ile Asp Trp Leu Trp Gly Gly Leu Asn Tyr Gln Ile
370                 375                 380

Glu His His Leu Phe Pro Thr Met Pro Arg Cys Asn Leu Asn Ala Cys
385                 390                 395                 400

Met Lys Tyr Val Lys Glu Trp Cys Lys Glu Asn Asn Leu Pro Tyr Leu
                405                 410                 415

Val Asp Asp Tyr Phe Asp Gly Tyr Ala Met Asn Leu Gln Gln Leu Lys
                420                 425                 430

Asn Met Ala Glu His Ile Gln Ala Lys Ala Ala
            435                 440

<210> SEQ ID NO 15
<211> LENGTH: 448
<212> TYPE: PRT
<213> ORGANISM: Borago officinalis

<400> SEQUENCE: 15

Met Ala Ala Gln Ile Lys Lys Tyr Ile Thr Ser Asp Glu Leu Lys Asn
1               5                   10                  15

His Asp Lys Pro Gly Asp Leu Trp Ile Ser Ile Gln Gly Lys Ala Tyr
            20                  25                  30

Asp Val Ser Asp Trp Val Lys Asp His Pro Gly Gly Ser Phe Pro Leu
        35                  40                  45

Lys Ser Leu Ala Gly Gln Glu Val Thr Asp Ala Phe Val Ala Phe His
    50                  55                  60

Pro Ala Ser Thr Trp Lys Asn Leu Asp Lys Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Ser Lys Met Gly Leu Tyr Asp Lys Lys Gly His Ile
                100                 105                 110

Met Phe Ala Thr Leu Cys Phe Ile Ala Met Leu Phe Ala Met Ser Val
            115                 120                 125

Tyr Gly Val Leu Phe Cys Glu Gly Val Leu Val His Leu Phe Ser Gly
        130                 135                 140

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175

Gly Ile Phe Ala Ala Asn Cys Leu Ser Gly Ile Ser Ile Gly Trp Trp
                180                 185                 190

Lys Trp Asn His Asn Ala His His Ile Ala Cys Asn Ser Leu Glu Tyr
            195                 200                 205

Asp Pro Asp Leu Gln Tyr Ile Pro Phe Leu Val Val Ser Ser Lys Phe
        210                 215                 220

Phe Gly Ser Leu Thr Ser His Phe Tyr Glu Lys Arg Leu Thr Phe Asp
```

```
                225                 230                 235                 240
Ser Leu Ser Arg Phe Phe Val Ser Tyr Gln His Trp Thr Phe Tyr Pro
                245                 250                 255

Ile Met Cys Ala Ala Arg Leu Asn Met Tyr Val Gln Ser Leu Ile Met
                260                 265                 270

Leu Leu Thr Lys Arg Asn Val Ser Tyr Arg Ala His Glu Leu Leu Gly
                275                 280                 285

Cys Leu Val Phe Ser Ile Trp Tyr Pro Leu Leu Val Ser Cys Leu Pro
                290                 295                 300

Asn Trp Gly Glu Arg Ile Met Phe Val Ile Ala Ser Leu Ser Val Thr
305                 310                 315                 320

Gly Met Gln Gln Val Gln Phe Ser Leu Asn His Phe Ser Ser Ser Val
                    325                 330                 335

Tyr Val Gly Lys Pro Lys Gly Asn Asn Trp Phe Glu Lys Gln Thr Asp
                340                 345                 350

Gly Thr Leu Asp Ile Ser Cys Pro Pro Trp Met Asp Trp Phe His Gly
                355                 360                 365

Gly Leu Gln Phe Gln Ile Glu His His Leu Phe Pro Lys Met Pro Arg
                370                 375                 380

Cys Asn Leu Arg Lys Ile Ser Pro Tyr Val Ile Glu Leu Cys Lys Lys
385                 390                 395                 400

His Asn Leu Pro Tyr Asn Tyr Ala Ser Phe Ser Lys Ala Asn Glu Met
                    405                 410                 415

Thr Leu Arg Thr Leu Arg Asn Thr Ala Leu Gln Ala Arg Asp Ile Thr
                420                 425                 430

Lys Pro Leu Pro Lys Asn Leu Val Trp Glu Ala Leu His Thr His Gly
                435                 440                 445
```

<210> SEQ ID NO 16
<211> LENGTH: 449
<212> TYPE: PRT
<213> ORGANISM: Mortierella alpina

<400> SEQUENCE: 16

```
Met Gly Thr Asp Gln Gly Lys Thr Phe Thr Trp Glu Glu Ile Ala Ala
1               5                   10                  15

His Asn Thr Lys Gly Asp Ile Phe Leu Ala Ile Thr Gly Arg Val Tyr
                20                  25                  30

Asp Val Thr Lys Phe Leu Ser Arg His Pro Gly Gly Val Asp Thr Ile
                35                  40                  45

Leu Leu Gly Ala Gly Arg Asp Val Thr Pro Val Phe Glu Met Tyr His
                50                  55                  60

Ala Phe Gly Ala Ala Asp Ala Ile Met Lys Lys Tyr Tyr Val Gly Thr
65                  70                  75                  80

Leu Val Ser Asn Phe Leu Pro Val Phe Pro Glu Pro Thr Val Phe His
                85                  90                  95

Lys Thr Leu Lys Thr Arg Val Glu Gly Tyr Phe Thr Asp Arg Asp Ile
                100                 105                 110

Asp Pro Lys Asn Arg Pro Glu Thr Trp Gly Arg Tyr Ala Leu Ile Phe
                115                 120                 125

Gly Ser Leu Ile Ala Ser Tyr Tyr Ala Gln Leu Glu Val Val Glu Arg
                130                 135                 140

Thr Trp Leu Gln Val Val Phe Ala Ile Ile Met Gly Phe Ala Cys Ala
145                 150                 155                 160
```

```
Gln Val Gly Leu Asn Pro Leu His Asp Ala Ser His Pro Asp Val Thr
                165                 170                 175
His Asn Pro Thr Val Trp Lys Thr Leu Gly Ala Thr His Asp Phe Asp
            180                 185                 190
Asn Gly Ala Ser Tyr Leu Val Trp Met Tyr Gln His Met Leu Gly His
        195                 200                 205
His Pro Tyr Thr Asn Ile Ala Gly Ala Asp Pro Asp Val Ser Thr Glu
    210                 215                 220
Glu Pro Asp Val Arg Thr Lys Arg Asn Gln Lys Trp Phe Val Asn His
225                 230                 235                 240
Ile Asn Gln Asp Met Phe Val Pro Phe Leu Tyr Gly Leu Leu Ala Phe
                245                 250                 255
Lys Val Arg Ile Gln Asp Ile Asn Ile Ile Tyr Phe Val Lys Thr Asn
            260                 265                 270
Asp Ala Ile Arg Val Asn Pro Ile Ser Thr Trp His Thr Val Met Phe
        275                 280                 285
Trp Gly Gly Lys Ala Phe Phe Val Tyr Arg Leu Ile Val Pro Leu Gln
    290                 295                 300
Tyr Leu Pro Leu Gly Lys Val Ile Leu Leu Glu Thr Val Ala Asp Met
305                 310                 315                 320
Val Ser Ser Tyr Trp Leu Ala Leu Thr Phe Gln Ala Asn His Val Met
                325                 330                 335
Glu Glu Val Gln Trp Pro Leu Pro Asp Glu Asn Gly Ile Ile Gln Lys
            340                 345                 350
Asp Trp Ala Ala Met Gln Val Glu Thr Thr Gln Asp Tyr Ala His Asp
        355                 360                 365
Ser His Leu Trp Thr Ser Ile Thr Gly Ser Leu Asn Tyr Gln Ala Val
    370                 375                 380
His His Leu Phe Pro Asn Val Ser Gln His His Thr Pro Asn Val Ser
385                 390                 395                 400
Gln His His Tyr Pro Asp Ile Leu Ala Ile Ile Lys Asn Thr Gln Ser
                405                 410                 415
Ser Tyr Lys Val Pro Tyr Leu Val Lys Asp Thr Phe Trp Gln Ala Gly
            420                 425                 430
Ala Ser His Leu Glu His Leu Arg Val Leu Gly Ile Arg Pro Lys Glu
        435                 440                 445
Glu

<210> SEQ ID NO 17
<211> LENGTH: 5
<212> TYPE: PRT
<213> ORGANISM: artificial sequence
<220> FEATURE:
<223> OTHER INFORMATION: Consensus sequence
<220> FEATURE:
<221> NAME/KEY: MISC_FEATURE
<222> LOCATION: (1)..(5)
<223> OTHER INFORMATION: Histidine box
<220> FEATURE:
<221> NAME/KEY: MISC_FEATURE
<222> LOCATION: (2)..(4)
<223> OTHER INFORMATION: Xaa = any amino acid

<400> SEQUENCE: 17

His Xaa Xaa Xaa His
1               5
```

DESATURASES AND METHODS OF USING THEM FOR SYNTHESIS OF POLYUNSATURATED FATTY ACIDS

CROSS REFERENCE TO RELATED APPLICATIONS

This is a divisional of U.S. patent application Ser. No. 14/308,456, filed Jun. 18, 2014, now U.S. Pat. No. 9,695,450, issued Jul. 4, 2017, which is a divisional of U.S. patent application Ser. No. 13/406,248, filed Feb. 27, 2012, now U.S. Pat. No. 8,791,327, issued Jul. 29, 2014; which is a continuation of U.S. patent application Ser. No. 12/141,865, filed Jun. 18, 2008, now U.S. Pat. No. 8,124,838 on Feb. 28, 2012; which is a divisional of U.S. patent application Ser. No. 10/975,692, filed Oct. 26, 2004, now U.S. Pat. No. 7,402,735, issued Jul. 22, 2008; which is a divisional of U.S. patent application Ser. No. 09/857,583, filed Aug. 17, 2001, now U.S. Pat. No. 6,825,017, issued Nov. 30, 2004; which is the U.S. National Stage of International Application No. PCT/US99/28655, filed Dec. 6, 1999; and which claims the benefit of U.S. Provisional Application No. 60/111,301, filed Dec. 7, 1998. All of these are incorporated herein by reference.

STATEMENT OF GOVERNMENTAL INTEREST

This work was supported by funds from the U.S. Department of Agriculture under NRICGP contract numbers 95-37301-2287 and 97-35301-4426. The United States government has certain rights in this invention.

INCORPORATION-BY-REFERENCE OF MATERIAL SUBMITTED AS AN ASCII TEXT FILE

A Sequence Listing is submitted herewith as an ASCII compliant text file named "Sequence_Listing.txt", created on Jun. 13, 2017, and having a size of 26,125 bytes, as permitted under 37 CFR 1.821(c). The material in the aforementioned file is hereby incorporated by reference in its entirety.

FIELD OF THE INVENTION

The invention relates to desaturase enzymes that can be used to produce polyunsaturated fatty acids with important dietary applications.

BACKGROUND

Fatty acids are fundamental components of living systems. They make up the major component of cytoplasmic membranes, common to plants, animals and protists alike.

Fatty acids of 20 carbons, with more than one unsaturated carbon-carbon bond along the hydrocarbon chain, are known to be of particular importance. Arachidonate (20:4) (Heinz, *Lipid Metabolism in Plants*, pp. 33-89, 1993; Yamazaki et al. *Biochim. Biophys. Acta* 1123:18-26, 1992; Ulsamer et al., *J. Cell Biol.* 43:105-114, 1969; and Albert et al. *Lipids* 14:498-500, 1979) and eicosapentaenoate (20:5) (Heinz, *Lipid Metabolism in Plants*, pp. 33-89, 1993; Yamazaki et al., *Biochim. Biophys. Acta* 1123:18-26, 1992; Ulsamer et al. *J. Cell Biol.* 43:105-114, 1969; and Cook et al., *J. Lipid Res.* 32:1265-1273, 1991), commonly referred to as EPA, are significant components of mammalian cell membranes and are also precursors of signal molecules including prostaglandins. Certain specialized mammalian tissues such as brain (Naughton, *J. Biochem.* 13:21-32, 1981), testes (Wilder and Coniglio, *Proc. Soc. Exp. Biol. Med.* 177:399-405, 1984), and retina (Aveldano de Caldironi et al., *Prog. Lipid Res.* 20:49-57, 1981) are especially rich in unsaturated fatty acids.

Arachidonate and eicosapentaenoate serve both as precursors for synthesis of 22-carbon polyunsaturated fatty acids and, with dihomo-γ-linoleate (20:3) (Yamazaki et al., *Biochim. Biophys. Acta* 1123:18-26, 1992; Ulsamer et al., *J. Cell Biol.* 43:105-114, 1969; and Albert et al., *Lipids* 14:498-500, 1979), as precursors to the synthesis of eicosanoid metabolic regulators (Hwang, *Fatty Acids in Foods and Their Health Implications*, 545-557, 1992). Key enzymes in the synthesis of 20-carbon fatty acids are desaturases, which introduce cis double bonds by removing two hydrogen atoms at specific locations along the aliphatic hydrocarbon chains. Desaturase enzymes are specific to the position, number, and stereochemistry of the double bonds already present in the target fatty acid (Heinz, *Lipid Metabolism in Plants*, 33-89, 1993).

To synthesize 20-carbon polyunsaturated fatty acids, mammals must acquire the essential fatty acids 18:2 (Brenner, *The Role of Fats in Human Nutrition*, pp. 45-79, 1989) and 18:3 (Nelson, *Fatty Acids in Foods and Their Health Implications*, pp. 437-471, 1992; Brenner, *The Role of Fats in Human Nutrition*, pp. 45-79, 1989; and Hulanicka et al. *J. Biol. Chem.* 239:2778-2787, 1964) from their diet (Nelson, *Fatty Acids in Foods and Their Health Implications*, 437-471, 1992). These dietary polyunsaturated fatty acids are metabolized in the endoplasmic reticulum by an alternating series of position-specific desaturases and malonyl-CoA-dependent chain-elongation steps (FIG. 1A), which results in the characteristic methylene-interrupted double bond pattern. In the liver, which is the primary organ of human lipid metabolism, the first step in biosynthesis of 20-carbon fatty acids is desaturation of the essential fatty acids at the $\Delta^6$ position. The desaturation products are elongated to 20:3 and 20:4 (Cook et al., *J. Lipid Res.* 32:1265-1273, 1991). In turn, these 20-carbon products are desaturated by a $\Delta^5$-desaturase to produce arachidonate and eicosapentaenoate. The $\Delta^6$-desaturation step is rate-limiting in this metabolic pathway (Bernet and Sprecher, *Biochim. Biophys. Acta* 398:354-363, 1975; and Yamazaki et al., *Biochim. Biophys. Acta* 1123:18-26, 1992) and, not surprisingly, is subject to regulation by dietary and hormonal changes (Brenner, *The Role of Fats in Human Nutrition*, pp. 45-79, 1989).

In contrast to the liver, an alternate pathway for biosynthesis of 20-carbon polyunsaturated fatty acids has been demonstrated in a few organisms and tissues (FIG. 1B). Instead of desaturation, the first step in the alternate pathway is elongation of the essential 18-carbon fatty acids to 20-carbon chain lengths, producing 20:2 (Ulsamer et al., *J. Cell Biol.* 43:105-114, 1969; and Albert et al. *Lipids* 14:498-500, 1979) and 20:3. Subsequent desaturation occurs via a $\Delta^8$-desaturase (FIG. 1). The products of this elongation-desaturation, 20:3 and 20:4, are the same as the more usual desaturation-elongation pathway. The $\Delta^8$ pathway is present in the soil amoebae *Acanthamoeba* sp. (Ulsamer et al, *J. Cell Biol.* 43:105-114, 1969), and in euglenoid species, where it is the dominant pathway for formation of 20-carbon polyunsaturated fatty acids (Hulanicka et al., *Journal of Biological Chemistry* 239:2778-2787, 1964).

This $\Delta^8$-desaturation pathway occurs in mammals, both in rat testis (Albert and Coniglio, *Biochim. Biophys. Acta*

489:390-396, 1977) and in human testis (Albert et al., *Lipids* 14:498-500, 1979). While $\Delta^8$ activity has been observed in breast cancer cell lines (Grammatikos et al., *Br. J. Cancer* 70:219-227, 1994; and Bardon et al., *Cancer Lett.* 99:51-58, 1996) and in glioma (Cook et al., *J. Lipid Res.* 32:1265-1273, 1991), no $\Delta^8$ activity is detectable in a corresponding non-cancerous breast cell line (Grammatikos et al., *Br. J. Cancer* 70:219-227, 1994) or in the brain (Dhopeshwarkar and Subramanian, *J. Neurochem.* 36:1175-1179, 1976). The significance of $\Delta^8$-desaturation to normal or cancer cell metabolism is unclear, since analysis of desaturase activities in mammalian systems is frequently complicated by the presence of competing $\Delta^6$ reactions and chain-shortening retroconversion of fatty acid substrates in tissue (Sprecher and Lee, *Biochim. Biophys. Acta* 388:113-125, 1975; Geiger et al., *Biochim. Biophys. Acta* 1170:137-142, 1993).

Polyunsaturated 20-carbon fatty acids are, for the reasons outlined above, important in the human diet, and there has been considerable recent interest in incorporating such fatty acids into infant food, baby formula, dietary supplements, and nutraceutical formulations.

It would therefore be desirable to produce new transgenic plants and animals with enhanced ability to produce polyunsaturated 20-carbon fatty acids.

SUMMARY OF THE DISCLOSURE

The invention provides novel $\Delta^5$-(FIG. 6A) and $\Delta^8$-(FIG. 7A) desaturase enzymes that may be cloned and expressed in the cells of various organisms, including plants, to produce 20-carbon polyunsaturated fatty acids. Expression of such fatty acids enhances the nutritional qualities of such organisms. For instance, oil-seed plants may be engineered to incorporate the $\Delta^5$- and $\Delta^8$-desaturases of the invention. Such oil-seed plants would produce seed-oil rich in polyunsaturated 20:3, 20:4, 20:5, 22:4, and 22:5 fatty acids. Such fatty acids could be incorporated usefully into infant formula, foods of all kinds, dietary supplements, nutraceutical, and pharmaceutical formulations.

The invention also provides proteins differing from the proteins of FIG. 6A and FIG. 7A by one or more conservative amino acid substitutions. Also provided are proteins that exhibit "substantial similarity" (defined in the "Definitions" section) with the proteins of FIG. 6A and FIG. 7A.

The invention provides isolated novel nucleic acids that encode the above-mentioned proteins, recombinant nucleic acids that include such nucleic acids and cells, and plants and organisms containing such recombinant nucleic acids.

The novel $\Delta^5$- and $\Delta^8$-desaturase enzymes can be used individually, or in conjunction with one another, for instance in a metabolic pathway, to produce polyunsaturated fatty acids, such as 20:3, 20:4, 20:5, 22:4, and 22:5 fatty acids.

The scope of the invention also includes portions of nucleic acids encoding the novel $\Delta^5$- and $\Delta^8$-desaturase enzymes, portions of nucleic acids that encode polypeptides substantially similar to these novel enzymes, and portions of nucleic acids that encode polypeptides that differ from the proteins of FIG. 6A and FIG. 7A by one or more conservative amino acid substitutions. Such portions of nucleic acids may be used, for instance, as primers and probes for research and diagnostic purposes. Research applications for such probes and primers include the identification and cloning of related $\Delta^5$- and $\Delta^8$-desaturases in other organisms including humans.

The invention also includes methods that utilize the $\Delta^5$- and/or the $\Delta^8$-desaturase enzymes of the invention. An example of this embodiment is a yeast or plant cell that carries genes for one or both desaturases of the invention and that, by virtue of these desaturases, is able to produce arachidonic acid and/or EPA.

BRIEF DESCRIPTION OF THE DRAWINGS

FIG. 1A shows a common pathway for synthesis of 20-carbon polyunsaturated fatty acids that begins with $\Delta^6$ desaturation of 18-carbon fatty acids followed by 2-carbon elongation, and then further desaturation and elongation.

FIG. 1B shows an alternate pathway that begins with an elongation of 18-carbon fatty acid to 20-carbon fatty acids, followed by $\Delta^8$ desaturation and a second desaturation at the $\Delta^5$ position.

FIG. 3 shows amino acid sequence similarities between the *Euglena* $\Delta^8$-desaturase protein (EFD1) (SEQ ID NO: 4) and the desaturase enzymes of *C. elegans*. The deduced amino acid sequence of the EFD1 gene shows similarity with the *C. elegans* $\Delta^6$ (FAT-3) (SEQ ID NO: 14) and $\Delta^5$ (FAT-4) (SEQ ID NO: 2) desaturases (Napier et al., *Biochem. J.* 330:611-614, 1998). The similarity is strongest in the regions of conserved function. In the N-terminal region amino acids forming a cytochrome $b_5$-like domain (Lederer, *Biochimie* 76:674-692, 1994) are indicated. The His-box motifs indicated by underlined characters are present in other identified membrane desaturases (Napier et al., *Biochem. J.* 330:611-614, 1998; Michaelson et al., *J. Biol. Chem.* 273:19055-19059, 1998; and Shanklin and Cahoon, *Annu. Rev. Plant Physiol. Plant Mol. Biol.* 48:611-641, 1998).

FIG. 6A shows the primary amino acid sequence of the fatty acid $\Delta^5$-desaturase from *Caenorhabditis elegans* (SEQ ID NO: 2).

FIG. 6B shows a nucleotide sequence including the ORF (open reading frame) that encodes the fatty acid $\Delta^5$-desaturase from *Caenorhabditis elegans* (SEQ ID NO: 1).

FIG. 7A shows the primary amino acid sequence of the fatty acid $\Delta^8$-desaturase from the protist *Euglena gracilis* (SEQ ID NO: 4).

FIG. 7B shows a nucleotide sequence including the ORF that encodes the $\Delta^8$-desaturase from the protist *Euglena gracilis* (SEQ ID NO: 3).

FIG. 9 shows a comparison of the predicted amino acid sequences of the borage $\Delta^6$-desaturase (bord6) (SEQ ID NO: 15), *C. elegans* FAT-3 (fat3) (SEQ ID NO: 14), *C. elegans* FAT-4 (fat4) (SEQ ID NO: 2), and the *Mortierella alpina* $\Delta^5$-(mord5) (SEQ ID NO: 16) desaturase. Identical or conserved residues are shaded, and the conserved HPGG heme-binding domain and the conserved histidine boxes are underlined. Abbreviations: bord6=*Borago officinalis* $\Delta^6$-desaturase (GenBank accession number U79010); fat4=*C. elegans* FAT-4 desaturase; fat3=*C. elegans* $\Delta^6$ desaturase sequence of W08D2.4 (GenBank accession number Z70271), edited to remove amino acids 38-67, on the basis of the cDNA sequence; mord5=*Mortierella alpina* $\Delta^5$ desaturase (GenBank accession number AF054824).

FIGS. 11A and 11B show the novel desaturation products from substrates lacking a $\Delta^8$ double bond. (A) Partial GC trace of fatty acid methyl esters derived from yeast expressing the fat-4 $\Delta^5$-desaturase supplemented with 20:2$\Delta^{11,14}$ (14.81 min.). The desaturation product of this substrate elutes at 14.62 min. and has been identified as 20:3$\Delta^{5,11,14}$. (B) Partial GC trace of yeast expressing the fat-4 $\Delta^5$-desaturase supplemented with 20:3$\Delta^{11,14,17}$ (14.87 min.). The desaturation product of this substrate elutes at 14.69 min. and has been identified as 20:4$\Delta^{5,11,14,17}$.

FIG. 12 is a table comparing the substrate specificities of *C. elegans* $\Delta^5$- and $\Delta^6$-desaturases.

FIG. 13 is a table comparing incorporation and desaturation of fatty acids by yeast strains transformed with a control construct pYES, and with pYES-541, a clone containing EGD1, the *E. gracilis* $\Delta^8$-desaturase gene. *S. cerevisiae* strains containing a control vector (pYES) or expressing EFD1 (pYES-541) were cultured in the presence of the indicated fatty acids. The cultures were harvested, washed, and methyl esters prepared from total cells and analyzed by GC. The weight % of total fatty acid methyl esters is indicated.

SEQUENCE LISTING

Figure 1C:
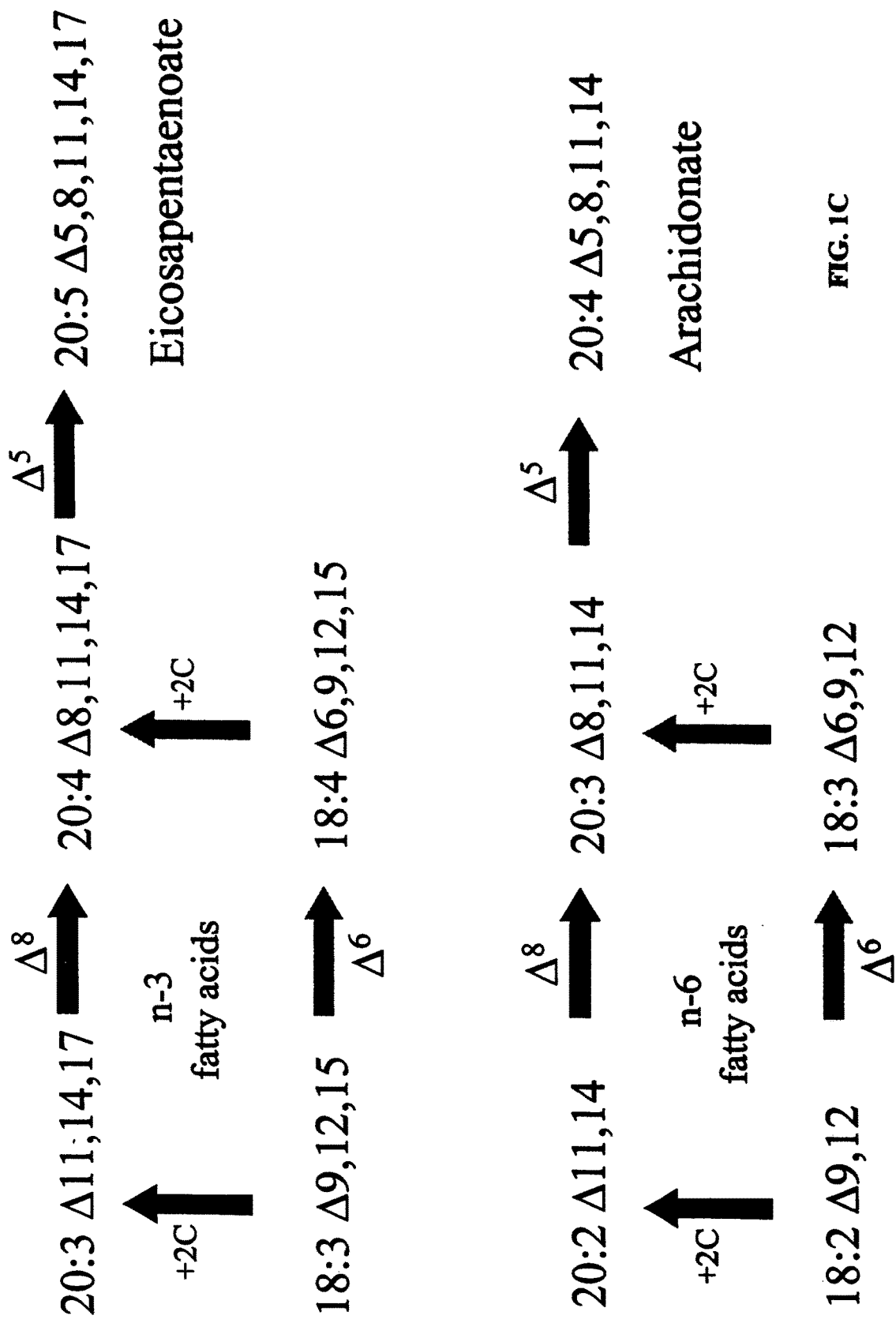
FIG. 1C shows alternate pathways for the synthesis of polyunsaturated fatty acids using $\Delta^5$-, $\Delta^6$-, and $\Delta^8$-desaturases to produce arachidonic acid and EPA.

The nucleic and amino acid sequences listed in the accompanying sequence listing are shown using standard letter abbreviations for nucleotide bases, and three-letter code for amino acids. Only one strand of each nucleic acid sequence is shown, but the complementary strand is understood to be included by any reference to the displayed strand.

SEQ ID NO: 1 is the nucleotide sequence corresponding to the open reading frame of the fatty acid $\Delta^5$-desaturase from *Caenorhabditis elegans*.

SEQ ID NO: 2 is the primary amino acid sequence of the fatty acid $\Delta^5$-desaturase from *Caenorhabditis elegans*.

SEQ ID NO: 3 is the nucleotide sequence corresponding to the open reading frame of the fatty acid $\Delta^8$-desaturase from the protist *Euglena gracilis*.

SEQ ID NO: 4 is the primary amino acid sequence of fatty acid $\Delta^8$-desaturase from the protist *Euglena gracilis*.

SEQ ID NOs: 5-8 are primers used to amplify and clone the $\Delta^8$-desaturase-encoding nucleic acid sequence.

SEQ ID NO: 9 is a polyadenylation signal.

SEQ ID NO: 10 is a primer used to amplify and clone the $\Delta^5$-desaturase-encoding nucleic acid sequence.

SEQ ID NO: 11 is a short RNA leader sequence.

SEQ ID NO: 12 is the amino acid sequence of a histidine box motif.

SEQ ID NO: 13 is the amino acid sequence of a histidine box motif.

SEQ ID NO: 14 is the primary amino acid sequence of the fatty acid $\Delta^6$-desaturase from *C. elegans*.

SEQ ID NO: 15 is the primary amino acid sequence of the fatty acid $\Delta^6$-desaturase from *Borago officinalis*.

SEQ ID NO: 16 is the primary amino acid sequence of the fatty acid $\Delta^5$-desaturase from *Mortierella alpina*.

SEQ ID NO: 17 is the amino acid sequence of a histidine box motif.

DESCRIPTION OF THE INVENTION

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, Genes VI, Oxford University Press: New York, 1997. The nomenclature for DNA bases as set forth at 37 C.F.R. § 1.822 is used. The standard one- and three-letter nomenclature for amino acid residues is used.

Definitions

Portion: A portion of a nucleic acid molecule is a stretch of contiguous nucleic acids corresponding to the sequence of that molecule that may be about 15, 20, 30, 40, 50, or 60 nucleic acids in length. Such nucleotide portions may be used as probes or primers. A portion of a protein is a stretch of contiguous amino acids corresponding to the amino acid sequence of that protein that may be about 5, 10, 20, 30, 40, or 50 residues in length. As used herein, such a portion may correspond to any segment of a nucleic acid molecule, for instance such a portion may correspond to a segment consisting of nucleotides 1-500, 501-1000, or 1001-1451 of the sequence shown in FIG. 6B, or nucleotides 1-400, 401-800, 801-1251 of the sequence shown in FIG. 7B.

Desaturase: A desaturase is an enzyme that promotes the formation of carbon-carbon double bonds in a hydrocarbon molecule.

Desaturase activity may be demonstrated by assays in which a preparation containing an enzyme is incubated with a suitable form of substrate fatty acid and analyzed for conversion of this substrate to the predicted fatty acid product. Alternatively, a DNA sequence proposed to encode a desaturase protein may be incorporated into a suitable vector construct and thereby expressed in cells of a type that do not normally have an ability to desaturate a particular fatty acid substrate. Activity of the desaturase enzyme encoded by the DNA sequence can then be demonstrated by supplying a suitable form of substrate fatty acid to cells transformed with a vector containing the desaturase-encoding DNA sequence and to suitable control cells (for example, transformed with the empty vector alone). In such an experiment, detection of the predicted fatty acid product in cells containing the desaturase-encoding DNA sequence and not in control cells establishes the desaturase activity. Examples of this type of assay have been described in, for example, Lee et al., *Science* 280:915-918, 1998; Napier et al., *Biochem. J.* 330:611-614, 1998; and Michaelson et al., *J. Biol. Chem.* 273:19055-19059, 1998, which are incorporated herein by reference.

The $\Delta^5$-desaturase activity may be assayed by these techniques using, for example, $20:3\Delta^{8,11,14}$ as substrate and detecting $20:4\Delta^{5,8,11,14}$ as the product (Michaelson et al., *J. Biol. Chem.* 273:19005-19059, 1998). Other potential substrates for use in $\Delta^5$ activity assays include (but are not limited to) $10:2\Delta^{11,14}$ (yielding $20:5\Delta^{5,11,14}$ as the product) and $20:30^{11,14,12}$ (yielding $20:40^{5,11,14,17}$ as the product).

The $\Delta^8$-desaturase may be assayed by similar techniques using, for example, $20:3\Delta^{11,14,17}$ as the substrate and detecting $20:4\Delta^{8,11,14,17}$ as the product.

ORF: Open reading frame. An ORF is a contiguous series of nucleotide triplets coding for amino acids. These sequences are usually translatable into a peptide.

Homologs: Two nucleotide or amino acid sequences that share a common ancestral sequence and diverged when a species carrying that ancestral sequence split into two species. Homologs frequently show a substantial degree of sequence identity.

Transformed: A transformed cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Purified: The term purified does not require absolute purity; rather, it is intended as a relative term. Thus, for example, a purified protein preparation is one in which the subject protein or other substance is more pure than in its natural environment within a cell. Generally, a protein preparation is purified such that the protein represents at least 50% of the total protein content of the preparation.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame. If introns are present, the operably linked DNA sequences may not be contiguous.

Cell: A plant, animal, protist, bacterial, or fungal cell.

Sequence similarity: The similarity between two nucleic acids or two amino acid sequences is expressed in terms of percentage sequence identity. The higher the percentage sequence identity between two sequences, the more similar the two sequences are.

In the case of protein alignments, similarity is measured not only in terms of percentage identity, but also takes into account conservative amino acid substitutions. Such conservative substitutions generally preserve the hydrophobicity and acidity of the substituted residue, thus preserving the structure (and therefore function) of the folded protein. The computer programs used to calculate protein similarity employ standardized algorithms that, when used with standardized settings, allow the meaningful comparison of similarities between different pairs of proteins.

Sequences are aligned, with allowances for gaps in alignment, and regions of identity are quantified using a computerized algorithm. Default parameters of the computer program are commonly used to set gap allowances and other variables.

Methods of alignment of sequences for comparison are well-known in the art. Various programs and alignment algorithms are described by Pearson et al., *Methods in Molecular Biology* 24: 307-331, 1994, and in Altschul et al., *Nature Genet.* 6:119-129, 1994. Altschul et al. presents a detailed consideration of sequence alignment methods and homology calculations.

The NCBI Basic Local Alignment Search Tool (BLAST™) (Altschul et al., *J. Mol. Biol.* 215:403-410, 1990) is available from several sources, including the National Center for Biotechnology Information (NBCI, Bethesda, Md.) and on the Internet, for use in connection with the sequence analysis programs blastp, blastn, blastx, tblastn and tblastx. BLAST™ can be assessed by the web site with the host name "www" and the domain name of "ncbi.nlm.nih.gov". A description of how to determine sequence identity using this program is available at the web site. As used herein, sequence identity is commonly determined with the BLAST™ software set to default parameters. For instance, blastn (version 2.0) software may be used to determine sequence identity between two nucleic acid sequences using default parameters (expect=10, matrix=BLOSUM62, filter=DUST (Tatusov and Lipmann, in preparation as of Dec. 1, 1999; and Hancock and Armstrong, *Comput. Appl. Biosci.* 10:67-70, 1994), gap existence cost=11, per residue gap cost=1, and lambda ratio=0.85). For comparison of two polypeptides, blastp (version 2.0) software may be used with default parameters (expect 10, filter=SEG (Wootton and Federhen, Computers in Chemistry 17:149-163, 1993), matrix=BLOSUM62, gap existence cost=11, per residue gap cost=1, lambda=0.85).

When aligning short peptides (fewer than around 30 amino acids), the alignment should be performed using the Blast 2 sequences function, employing the PAM30 matrix set to default parameters (open gap 9, extension gap 1 penalties).

An alternative alignment tool is the ALIGN Global Optimal Alignment tool (version 3.0) available from Biology Workbench online at biology.ncsa.uiuc.edu. This tool may be used with settings set to default parameters to align two known sequences. References for this tool include Meyers and Miller, *CABIOS* 4:11-17, 1989.

Conservative amino acid substitutions are those substitutions that, when made, least interfere with the properties of the original protein, i.e., the structure and especially the function of the protein is conserved and not significantly changed by such substitutions. The table below shows amino acids that may be substituted for an original amino acid in a protein and that are regarded as conservative substitutions.

TABLE 1

| Original Residue | Conservative Substitutions |
|---|---|
| ala | ser |
| arg | lys |
| asn | gln; his |
| asp | glu |
| cys | ser |
| gln | asn |
| glu | asp |
| gly | pro |
| his | asn; gln |
| ile | leu; val |
| leu | ile; val |
| lys | arg; gln; glu |
| met | leu; ile |
| phe | met; leu; tyr |
| ser | thr |
| thr | ser |
| trp | tyr |
| tyr | trp; phe |
| val | ile; leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Probe: An isolated nucleic acid attached to a detectable label or reporter molecule. Typical labels include radioactive isotopes, ligands, chemiluminescent agents, and enzymes.

Primers: Short nucleic acids, preferably DNA oligonucleotides 10 nucleotides or more in length, that are annealable to a complementary target DNA strand by nucleic acid hybridization to form a hybrid between the primer and the target DNA strand, then extendable along the target DNA strand by a DNA polymerase enzyme. Primer pairs can be used for amplification of a nucleic acid sequence, e.g., by the polymerase chain reaction (PCR) or other nucleic-acid amplification methods known in the art.

Probes and primers as used in the present invention typically comprise at least 15 contiguous nucleotides. In order to enhance specificity, longer probes and primers may also be employed, such as probes and primers that comprise at least 20, 30, 40, 50, 60, 70, 80, 90, 100, or 150 consecutive nucleotides of the disclosed nucleic acid sequences.

Alternatively, such probes and primers may comprise at least 15, 20, 30, 40, 50, 60, 70, 80, 90, 100, or 150 consecutive nucleotides that share a defined level of sequence identity with one of the disclosed sequences, for instance, at least a 50%, 60%, 70%, 80%, 90%, or 95% sequence identity.

Alternatively, such probes and primers may be nucleotide molecules that hybridize under specific conditions and remain hybridized under specific wash conditions such as those provided below. These conditions can be used to identifying variants of the desaturases. Nucleic acid molecules that are derived from the desaturase cDNA and gene sequences include molecules that hybridize under various conditions to the disclosed desaturase nucleic acid molecules, or fragments thereof. Generally, hybridization conditions are classified into categories, for example very high stringency, high stringency, and low stringency. The conditions for probes that are about 600 base pairs or more in length are provided below in three corresponding categories.

Very High Stringency (detects sequences that share 90% sequence identity)

| Hybridization | in | SSC | at | 65° C. | 16 hours |
|---|---|---|---|---|---|
| Wash twice | in | SSC | at | room temp. | 15 minutes each |
| Wash twice | in | SSC | at | 65° C. | 20 minutes each |

High Stringency (detects sequences that share 80% sequence identity or greater)

| Hybridization | in | SSC | at | 65° C.-70° C. | 16-20 hours |
|---|---|---|---|---|---|
| Wash twice | in | SSC | at | room temp. | 5-20 minutes each |
| Wash twice | in | SSC | at | 55° C.-70° C. | 30 minutes each |

Low Stringency (detects sequences that share greater than 50% sequence identity)

| Hybridization | in | SSC | at | room temp.-55° C. | 16-20 hours |
|---|---|---|---|---|---|
| Wash at least twice | in | SSC | at | room temp.-55° C. | 20-30 minutes each |

Methods for preparing and using probes and primers are described in the references, for example Sambrook et al. *Molecular Cloning: A Laboratory Manual*, $2^{nd}$ ed., Cold Spring Harbor Laboratory Press, N Y, 1989; Ausubel et al. *Current Protocols in Molecular Biology*, Greene Publishing Associates and Wiley-Intersciences, 1987; and Innis et al., *PCR Protocols, A Guide to Methods and Applications*, Academic Press, Inc., San Diego, Calif. 1990. PCR primer pairs can be derived from a known sequence, for example, by using computer programs intended for that purpose such as Primer (Version 0.5, 1991, Whitehead Institute for Biomedical Research, Cambridge, Mass.).

Recombinant nucleic acid: A sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques such as those described in Sambrook et al. *Molecular Cloning: A Laboratory Manual*, $2^{nd}$ ed., Cold Spring Harbor Laboratory Press, N Y, 1989. The term recombinant includes nucleic acids that have been altered solely by addition, substitution, or deletion of a portion of the nucleic acid.

Native: The term "native" refers to a naturally-occurring ("wild-type") nucleic acid or polypeptide. The native nucleic acid or protein may have been physically derived from a particular organism in which it is naturally occurring or may be a synthetically constructed nucleic acid or protein that is identical to the naturally-occurring nucleic acid or protein.

Isolated: An "isolated" nucleic acid is one that has been substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

Plant: The term "plant" encompasses any higher plant and progeny thereof, including monocots (e.g., corn, rice, wheat, barley, rapeseed, soy, sunflower, etc.), dicots (e.g., potato, tomato, etc.), and includes parts of plants, including seeds, fruit, tubers, etc.

The invention will be better understood by reference to the Examples herein. The scope of the invention is not to be considered limited thereto.

Description and General Methods of the Disclosure

The present invention utilizes standard laboratory practices for the cloning, manipulation, and sequencing of nucleic acids, the purification and analysis of proteins, and other molecular biological and biochemical techniques, unless otherwise stipulated. Such techniques are explained in detail in standard laboratory manuals such as Sambrook et al., *Molecular Cloning: A Laboratory Manual, 2nd* ed., Cold Spring Harbor Laboratory Press, N Y, 1989; and Ausubel et al., *Current Protocols in Molecular Biology*, Green and Wiley-Interscience, N Y, 1987.

The inventors have identified, cloned, and expressed a novel fatty acid $\Delta^8$-desaturase from the protist *Euglena gracilis* and a novel fatty acid $\Delta^5$-desaturase from *Caenorhabditis elegans* that may be used together to produce polyunsaturated fatty acids.

The invention provides novel purified $\Delta^5$ and $\Delta^8$ proteins (FIG. 6A and FIG. 7A, respectively). The invention also provides proteins differing from the proteins of FIG. 6A and FIG. 7A by one or more conservative amino acid substitutions, as well as proteins that show "substantial similarity" with the proteins of FIG. 6A and FIG. 7A. Substantial similarity is defined in the "Definitions" section. Proteins of the invention include proteins that show at least 50% amino acid similarity with the proteins shown in FIG. 6A and FIG. 7A. The term "50% amino acid similarity" is objectively and consistently defined by use of blastp sequence analysis software set at default parameters. Proteins of the invention also include proteins showing at least 60%, at least 70%, at least 80%, at least 90%, and at least 95% similarity (to the sequences of FIG. 6A or FIG. 7A) using blastp with default parameters.

The invention provides isolated novel nucleic acids that encode the above-mentioned proteins, recombinant nucleic acids that include such nucleic acids and cells containing such recombinant nucleic acids. Nucleic acids of the invention thus include nucleic acids that encode: (1) amino acid sequences as shown in FIG. 6A and FIG. 7A; (2) amino acid sequences that differ from the sequences shown in FIG. 6A and FIG. 7A by one or more conservative amino acid substitutions; and (3) amino acid sequences that show at least 50% similarity (as measured by blastp at default parameters) with the sequence of FIG. 6A and FIG. 7A.

Nucleic acids of the invention also include nucleic acids that show at least the term "50% similarity" with the nucleic acids shown in FIG. 6B and FIG. 7B. The term "50% similarity" is objectively defined by the use of blastn software set at default perimeters. Nucleic acids of the invention also include nucleic acids showing at least 60%, at least 70%, at least 80%, at least 90%, and at least 95% similarity (to the sequences of FIG. 6B and FIG. 7B) using blastn with default perimeters.

The novel $\Delta^5$- and $\Delta^8$-desaturase enzymes can be used individually, or in conjunction with one another, for instance in a metabolic pathway, to produce polyunsaturated fatty acids, such as 20:3 and 20:4 fatty acids. FIG. 1B shows an example of such a metabolic pathway. Such a pathway may be engineered into any cell by use of appropriate expression systems. A simple way to provide such elements is by the use of commercially available expression systems, discussed in detail below.

The scope of the invention covers not only entire nucleic acids encoding the novel $\Delta^5$- and $\Delta^8$ desaturase enzymes (and substantially similar derivatives of such enzymes) but also covers "portions" of such nucleic acids (as defined in the "Definitions" section, herein). Such claimed portions are identified by their possession of a particular degree of similarity with similar sized portions of the nucleotides of FIG. 6B and FIG. 7B and may have a length of about 15, 20, 30, 40, or 50 contiguous nucleotides. Similarity is objectively measured by sequence comparison software, such as the "blastn" and "blastp" software available from the National Center for Biotechnology Information (NBCI, Bethesda, Md.) and on the Internet at the web site with the host name "www" and the domain name of "ncbi.nlm.nih.gov". Similarity between portions of nucleic acids claimed and similar sized portions of the nucleic acid sequences of FIG. 6B and FIG. 7B may be at least 50%, 60%, 70%, 80%, 90%, 95%, or even 98%. Such portions of nucleic acids may be used, for instance, as primers and probes for research and diagnostic purposes. Portions of nucleic acids may be selected from any area of the sequences shown in FIG. 6B or FIG. 7B, for instance the first, second, third, etc., group of 100 nucleic acids as numbered in the figures.

Recombinant nucleic acids, as mentioned above, may, for instance, contain all or portion of a disclosed nucleic acid operably linked to another nucleic acid element such as a promoter, for instance, as part of a clone designed to express a protein. Cloning and expression systems are commercially available for such purposes.

Various yeast strains and yeast-derived vectors are commonly used for expressing and purifying proteins, for example, *Pichia pastoris* expression systems are available from Invitrogen (Carlsbad, Calif.). Such systems include suitable *Pichia pastoris* strains, vectors, reagents, sequencing primers, and media. A similar system for expression of proteins in *Saccharomyces cerevisiae* is also available from Invitrogen, which includes vectors, reagents and media. For example, a nucleotide sequence (e.g., a gene coding for the $\Delta^5$- or $\Delta^8$-desaturase enzyme of the invention) may be cloned into the yeast expression vector pYES2 and expressed under the control of an inducible promoter, such as a galactose-inducible promoter (GAL1).

Non-yeast eukaryotic vectors may also be used for expression of the desaturases of the invention. Examples of such systems are the well known Baculovirus system, the Ecdysone-inducible mammalian expression system that uses regulatory elements from *Drosophila melanogaster* to allow control of gene expression, and the Sindbis viral expression system that allows high level expression in a variety of mammalian cell lines. These expression systems are also available from Invitrogen.

Standard prokaryotic cloning vectors may also be used, for example pBR322, pUC18 or pUC19 as described in Sambrook et al, 1989. Nucleic acids encoding the desaturases of the invention may be cloned into such vectors that may then be transformed into bacteria such as *Escherichia coli* (*E. coli*) which may then be cultured so as to express the protein of interest. Other prokaryotic expression systems include, for instance, the arabinose-induced pBAD expression system that allows tightly controlled regulation of expression, the IPTG-induced pRSET system that facilitates rapid purification of recombinant proteins and the IPTG-induced pSE402 system that has been constructed for optimal translation of eukaryotic genes. These three systems are available commercially from Invitrogen and, when used according to the manufacturer's instructions, allow routine expression and purification of proteins.

Alternatively, and of particular importance to this invention, a plant expression system could be used. Plant expression systems are commercially available. A gene of interest of the invention may be cloned into a vector and the construct used to transform a plant cell. Any well known vector suitable for stable transformation of plant cells and/or for the establishment of transgenic plants may be used, including those described in, e.g., Pouwels et al., *Cloning Vectors: A Laboratory Manual*, 1985, supp. 1987; Weissbach and Weissbach, *Methods for Plant Molecular Biology*, Academic Press, 1989; and Gelvin et al., *Plant Molecular Biology Manual*, Kluwer Academic Publishers, 1990. Such plant expression vectors can include expression control sequences (e.g., inducible or constitutive, environmentally or developmentally regulated, or cell- or tissue-specific expression-control sequences).

Examples of constitutive plant promoters useful for expressing desaturase enzymes in plants include, but are not limited to, the cauliflower mosaic virus (CaMV) 35S promoter (see, e.g., Odel et al., *Nature* 313:810, 1985; Dekeyser et al., *Plant Cell* 2:591, 1990; and Terada and Shimamoto, *Mol. Gen. Genet.* 220:389, 1990); the nopaline synthase promoter (An et al., *Plant Physiol.* 88:547, 1988) and the octopine synthase promoter (Fromm et al., *Plant Cell* 1:977, 1989).

A variety of plant-gene promoters that are regulated in response to environmental, hormonal, chemical, and/or developmental signals, also can be used for protein expression in plant cells, including promoters regulated by (1) heat (Callis et al., *Plant Physiol.* 88:965, 1988), (2) light (e.g., pea rbcS-3A promoter, Kuhlemeier et al., *Plant Cell* 1:471, 1989; maize rbcS promoter, Schaffner and Sheen, *Plant Cell* 3:997, 1991; or chlorophyll a/b-binding protein promoter, Simpson et al., *EMBO J.* 4:2723, 1985), (3) hormones, such as abscisic acid (Marcotte et al., *Plant Cell* 1:969, 1989), (4) wounding (e.g., wunI, Siebertz et al., *Plant Cell* 1:961, 1989); or (5) chemicals such as methyl jasmonate, salicylic acid, or a safener. It may also be advantageous to employ (6) organ-specific promoters (e.g., Roshal et al., *EMBO J.* 6:1155, 1987; Schernthaner et al., *EMBO J.* 7:1249, 1988; Bustos et al., *Plant Cell* 1:839, 1989; Zheng et al., *Plant J.* 4:357-366, 1993). Tissue-specific expression may be facilitated by use of certain types of promoters, for example, the napin promoter is a seed-storage protein promoter from *Brassica* and specific to developing seeds. The β-conglycinin promoters drive the expression of recombinant nucleic acids thus allowing, the $\Delta^5$ or $\Delta^8$ proteins of the invention to be expressed only in specific tissues, for example, seed tissues.

Plant expression vectors can include regulatory sequences from the 3'-untranslated region of plant genes (Thornburg et al., *Proc. Natl. Acad. Sci. USA* 84:744, 1987; An et al., *Plant Cell* 1:115, 1989), e.g., a 3' terminator region to increase mRNA stability of the mRNA, such as the PI-II terminator region of potato or the octopine or nopaline synthase 3' terminator regions.

Useful dominant selectable marker genes for expression in plant cells include, but are not limited to: genes encoding antibiotic-resistance genes (e.g., resistance to hygromycin, kanamycin, bleomycin, G418, streptomycin, or spectinomycin); and herbicide-resistance genes (e.g., phosphinothricin acetyltransferase). Useful screenable markers include, but are not limited to, β-glucuronidase and green fluorescent protein.

The invention also provides cells or plants or organisms transformed with recombinant nucleic acid constructs that include all or a portion of the newly discovered polynucleotides that encode the novel $\Delta^5$ and/or $\Delta^8$ desaturase enzymes. An example of such a transformed plant or organism would be a potato, tomato, rapeseed, sunflower, soy, wheat, or corn plant. Multi-celled fungi, such as edible mushrooms, may also be transformed. Transformed oil-seed plants are of particular interest as 20-carbon polyunsaturated fatty acids would accumulate within the seed-oil.

Nucleic acid constructs that express a nucleic acid according to the invention can be introduced into a variety of host cells or organisms in order to alter fatty acid biosynthesis. Higher plant cells, eukaryotic, and prokaryotic host cells all may be so transformed using an appropriate expression system as described above.

After a cDNA (or gene) encoding a desaturase has been isolated, standard techniques may be used to express the cDNA in transgenic plants in order to modify the particular plant characteristic. The basic approach is to clone the cDNA into a transformation vector, such that the cDNA is operably linked to control sequences (e.g., a promoter) directing expression of the cDNA in plant cells. The transformation vector is then introduced into plant cells by any of various techniques, for example by *Agrobacterium*-mediated transformation of plants or plant tissues, or by electroporation of protoplasts, and progeny plants containing the introduced cDNA are selected. All or part of the transformation vector stably integrates into the genome of the plant cell. That part of the transformation vector that integrates into the plant cell and that contains the introduced cDNA and associated sequences for controlling expression (the introduced "transgene") may be referred to as the "recombinant expression cassette."

Selection of progeny plants containing the introduced transgene may be made based upon the detection of an altered phenotype. Such a phenotype may result directly from the cDNA cloned into the transformation vector or may be manifested as enhanced resistance to a chemical agent (such as an antibiotic) as a result of the inclusion of a dominant selectable marker gene incorporated into the transformation vector.

Successful examples of the modification of plant characteristics by transformation with cloned cDNA sequences are replete in the technical and scientific literature. Selected examples, which serve to illustrate the knowledge in this field of technology include:

U.S. Pat. No. 5,571,706 ("Plant Virus Resistance Gene and Methods")

U.S. Pat. No. 5,677,175 ("Plant Pathogen Induced Proteins")

U.S. Pat. No. 5,510,471 ("Chimeric Gene for the Transformation of Plants")

U.S. Pat. No. 5,750,386 ("Pathogen-Resistant Transgenic Plants")
U.S. Pat. No. 5,597,945 ("Plants Genetically Enhanced for Disease Resistance")
U.S. Pat. No. 5,589,615 ("Process for the Production of Transgenic Plants with Increased Nutritional Value Via the Expression of Modified 2S Storage Albumins")
U.S. Pat. No. 5,750,871 ("Transformation and Foreign Gene Expression in *Brassica* Species")
U.S. Pat. No. 5,268,526 ("Overexpression of Phytochrome in Transgenic Plants")
U.S. Pat. No. 5,262,316 ("Genetically Transformed Pepper Plants and Methods for their Production")
U.S. Pat. No. 5,569,831 ("Transgenic Tomato Plants with Altered Polygalacturonase Isoforms")

These examples include descriptions of transformation vector selection, transformation techniques, and the construction of constructs designed to over-express the introduced cDNA. In light of the foregoing and the provision herein of the desaturase amino acid sequences and nucleic acid sequences, it is thus apparent that one of skill in the art will be able to introduce the cDNAs, or homologous or derivative forms of these molecules, into plants in order to produce plants having enhanced desaturase activity. Furthermore, the expression of one or more desaturases in plants may give rise to plants having increased production of poly-unsaturated fatty acids.

The invention also pertains to antibodies to the desaturase enzymes, and fragments thereof, these antibodies may be useful for purifying and detecting the desaturases. The provision of the desaturase sequences allows for the production of specific antibody-based binding agents to these enzymes.

Monoclonal or polyclonal antibodies may be produced to the desaturases, portions of the desaturases, or variants thereof. Optimally, antibodies raised against epitopes on these antigens will specifically detect the enzyme. That is, antibodies raised against the desaturases would recognize and bind the desaturases, and would not substantially recognize or bind to other proteins. The determination that an antibody specifically binds to an antigen is made by any one of a number of standard immunoassay methods; for instance, Western blotting, Sambrook et al. (ed.), *Molecular Cloning: A Laboratory Manual*, 2nd ed., Vols. 1-3, Cold Spring Harbor Laboratory Press, Cold Spring Harbor, N.Y., 1989.

To determine that a given antibody preparation (such as a preparation produced in a mouse against the $\Delta^5$-desaturase) specifically detects the desaturase by Western blotting, total cellular protein is extracted from cells and electrophoresed on a SDS-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of 5-bromo-4-chloro-3-indolyl phosphate/nitro blue tetrazolium results in the production of a densely blue-colored compound by immuno-localized alkaline phosphatase.

Antibodies that specifically detect a desaturase will, by this technique, be shown to bind substantially only the desaturase band (having a position on the gel determined by the molecular weight of the desaturase). Non-specific binding of the antibody to other proteins may occur and may be detectable as a weaker signal on the Western blot (which can be quantified by automated radiography). The non-specific nature of this binding will be recognized by one skilled in the art by the weak signal obtained on the Western blot relative to the strong primary signal arising from the specific anti-desaturase binding.

Antibodies that specifically bind to desaturases belong to a class of molecules that are referred to herein as "specific binding agents." Specific binding agents that are capable of specifically binding to the desaturase of the present invention may include polyclonal antibodies, monoclonal antibodies, and fragments of monoclonal antibodies such as Fab, F(ab')2, and Fv fragments, as well as any other agent capable of specifically binding to one or more epitopes on the proteins.

Substantially pure desaturase suitable for use as an immunogen can be isolated from transfected cells, transformed cells, or from wild-type cells. Concentration of protein in the final preparation is adjusted, for example, by concentration on an Amicon filter device, to the level of a few micrograms per milliliter. Alternatively, peptide fragments of a desaturase may be utilized as immunogens. Such fragments may be chemically synthesized using standard methods, or may be obtained by cleavage of the whole desaturase enzyme followed by purification of the desired peptide fragments. Peptides as short as three or four amino acids in length are immunogenic when presented to an immune system in the context of a Major Histocompatibility complex (MHC) molecule, such as MHC class I or MHC class II. Accordingly, peptides comprising at least 3 and preferably at least 4, 5, 6, or more consecutive amino acids of the disclosed desaturase amino acid sequences may be employed as immunogens for producing antibodies.

Because naturally occurring epitopes on proteins frequently comprise amino acid residues that are not adjacently arranged in the peptide when the peptide sequence is viewed as a linear molecule, it may be advantageous to utilize longer peptide fragments from the desaturase amino acid sequences for producing antibodies. Thus, for example, peptides that comprise at least 10, 15, 20, 25, or 30 consecutive amino acid residues of the amino acid sequence may be employed. Monoclonal or polyclonal antibodies to the intact desaturase, or peptide fragments thereof may be prepared as described below.

Monoclonal antibody to any of various epitopes of the desaturase enzymes that are identified and isolated as described herein can be prepared from murine hybridomas according to the classic method of Kohler & Milstein, *Nature* 256:495, 1975, or a derivative method thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol.* 70:419, 1980), or a derivative method thereof. Selected positive clones can be expanded and their monoclonal antibody product harvested for use. Detailed procedures for monoclonal antibody production are described in Harlow & Lane, *Antibodies, A Laboratory Manual*, Cold Spring Harbor Laboratory, New York, 1988.

Polyclonal antiserum containing antibodies to heterogenous epitopes of a single protein can be prepared by immunizing suitable animals with the expressed protein, which can be unmodified or modified, to enhance immunogenicity. Effective polyclonal antibody production is affected by many factors related both to the antigen and the host species. For example, small molecules tend to be less immunogenic than other molecules and may require the use of carriers and an adjuvant. Also, host animals vary in response to site of inoculations and dose, with both inadequate and excessive doses of antigen resulting in low-titer antisera. Small doses (ng level) of antigen administered at multiple intradermal sites appear to be most reliable. An effective immunization protocol for rabbits can be found in Vaitukaitis et al., *J. Clin. Endocrinol. Metab.* 33:988-991, 1971.

Booster injections can be given at regular intervals, and antiserum harvested when the antibody titer thereof, as determined semi-quantitatively, for example, by double immunodiffusion in agar against known concentrations of the antigen, begins to fall. See, for example, Ouchterlony et al., *Handbook of Experimental Immunology*, Wier, D. (ed.), Chapter 19, Blackwell, 1973. A plateau concentration of antibody is usually in the range of 0.1 to 0.2 mg/mL of serum (about 12 µM). Affinity of the antisera for the antigen is determined by preparing competitive binding curves using conventional methods.

Antibodies may be raised against the desaturases of the present invention by subcutaneous injection of a DNA vector that expresses the enzymes in laboratory animals, such as mice. Delivery of the recombinant vector into the animals may be achieved using a hand-held form of the Biolistic system (Sanford et al., *Particulate Sci. Technol.* 5:27-37, 1987, as described by Tang et al., *Nature* (London) 356:153-154, 1992). Expression vectors suitable for this purpose may include those that express the cDNA of the enzyme under the transcriptional control of either the human β-actin promoter or the cytomegalovirus (CMV) promoter. Methods of administering naked DNA to animals in a manner resulting in expression of the DNA in the body of the animal are well known and are described, for example, in U.S. Pat. No. 5,620,896 ("DNA Vaccines Against Rotavirus Infections"); U.S. Pat. No. 5,643,578 ("Immunization by Inoculation of DNA Transcription Unit"); and U.S. Pat. No. 5,593,972 ("Genetic Immunization"), and references cited therein.

Antibody fragments may be used in place of whole antibodies and may be readily expressed in prokaryotic host cells. Methods of making and using immunologically effective portions of monoclonal antibodies, also referred to as "antibody fragments," are well known and include those described in Better & Horowitz, *Methods Enzymol.* 178: 476-496, 1989; Glockshuber et al. *Biochemistry* 29:1362-1367, 1990; and U.S. Pat. No. 5,648,237 ("Expression of Functional Antibody Fragments"); U.S. Pat. No. 4,946,778 ("Single Polypeptide Chain Binding Molecules"); and U.S. Pat. No. 5,455,030 ("Immunotherapy Using Single Chain Polypeptide Binding Molecules"), and references cited therein.

EXPERIMENTAL EXAMPLES

Example 1: Organism Strains and Culture

The strain *Euglena gracilis* Z was obtained from Columbia Scientific. The organism was cultured on Cramer and Meyers medium (Cramer, and Meyers, *Archiv fur Mikrobiologie* 17:384-402, 1952) with the addition of sucrose as a carbon source. Cultures were maintained at 25° C. in absolute darkness.

*C. elegans* was obtained from *Caenorhabditis* Genetics Center, St. Paul, Minn., and grown under standard conditions (Sulston et al., *The Nematode Caenorhabditis elegans* (Wood, W. B., Eds.), pp. 587-606, Cold Spring Harbor Laboratory Press, Cold Spring Harbor, N.Y., 1988).

Example 2: Database Searches for *C. elegans* Gene Homologs

The Sanger Center (http://www.sanger.ac.uk/projects/c_elegans/blast_server.shtml) *C. elegans* genomic database was searched using BLAST™ with sequences of plant desaturase enzymes, including the *B. officinalis* $\Delta^6$-desaturase (GenBank accession number U79010). Two *C. elegans* polypeptides with the highest scores were a peptide on cosmid W08D2 (high score 163), and one on T13F2 (high score 121).

Example 3: RNA Isolation, Reverse Transcription PCR, and RACE (Rapid Amplification of cDNA Ends)

For the *E. gracilis* $\Delta^8$ gene, total RNA was isolated from heterotrophic cultures of *E. gracilis* using a phenol-SDS protocol (Ausubel, *Current Protocols In Molecular Biology*, 1988). Messenger RNA was purified from total RNA using the PolyA-tract system (Promega Scientific, Madison, Wis.). Reverse transcription reactions were carried out using Superscript II (Life Technologies, Rockville, Md.). First-strand synthesis in the initial reactions was primed using anchored polyT primers (Clontech, Palo Alto, Calif.). Second-strand synthesis was conducted as described (Life Technologies), and polymerase chain reaction amplification of the core region of the gene was accomplished using the primers (GGCTGGCTGACNCAYGARTTYTGYCAY; SEQ. ID NO. 5) and (CATCGTTGGAAANARRTGRT-GYTCDATYTG; SEQ. ID NO. 6), designed to be completely degenerate to sequences overlapping the first and third His-box regions of the $\Delta^6$-desaturase *C. elegans* gene.

The amplification protocol was developed using published guidelines for use of degenerate primers (Compton, *PCR Protocols: A Guide To Methods And Applications*, 1990). The amplification consisted of 5 preliminary cycles at very low annealing temperature (30 seconds at 94° C., 1-minute ramp to 37° C., 45 seconds at 37° C., 3-minute ramp to 72° C.) followed by 30 cycles with higher temperature (30 seconds at 94° C., 1-minute ramp to 50° C., 45 seconds at 50° C., 3-minute ramp to 72° C. Preliminary amplifications to optimize thermal cycling parameters used Pfu DNA polymerase (Stratagene, La Jolla, Calif.). Amplification was successful at 3 mM magnesium and each primer at 4 Subsequently Taq polymerase was used for amplification under identical conditions.

Polymerase chain reaction products from 350 to 750 bp were isolated from agarose gels with commercial reagents (Qiagen, Valencia, Calif.) and sequenced directly using the degenerate primers and dye-termination sequencing technology (Applied Biosystems, Foster City, Calif.). A group of identical amplification products contained an open reading frame that was homologous to known desaturases when analyzed by BLAST™ search (Altschul et al., *Nucleic Acids Res.* 25:3389-3402, 1997). The 5' and 3' sequences of the complete mRNA were obtained with the Marathon RACE system (Clontech), using pairs of nested primers designed to amplify from within the core sequence. To clone the complete 5' end of the gene, it was necessary to repeat the reverse transcription with a primer specific to the sequence of the open reading frame and repeat the 5' RACE amplification.

For the *C. elegans* $\Delta^5$ gene, RNA isolation and reverse transcription-PCR were performed as follows. RT-PCR was used to amplify the coding sequences of the two putative desaturase genes. Total RNA from mixed stage *C. elegans* was used for the RT-PCR template. The nematodes were grown on agar plates as described and RNA was isolated using the phenol/SDS method (Sluder et al., *Dev. Biol.* 184:303-319, 1997). RT-PCR was performed using the Superscript™ One-Step RT-PCR system (Gibco-BRL/Life Technologies). Approximately 1 µg of total RNA was added to a reaction mixture consisting 0.2 mM of each dNTP, 1.2 mM MgSO$_4$, Superscript II™ RT/Taq polymerase mix, and 200 µM of appropriate downstream and upstream primers. The reactions were incubated at 50° C. for 30 min., then subject to 35 cycles of PCR amplification. For the T13F2.1 gene (fat-4) a 5' primer corresponding to bases 34339-34361 of cosmid T13F2 was used. SmaI, HindIII, and XhoI restriction sites were added to these sequences to facilitate cloning. The resulting primer (CCCGGGAAGCTTCTCGAG-GAATTTTCAATCCTCCTTGGGTC; SEQ. ID NO: 7) anneals to the cosmid T13F2 19-42 base pairs upstream of the putative start codon ATG of the fat-4 gene. To amplify the 3' end of the fat-4 gene, a primer was used corresponding to the inverse complement of bases 37075-37095 of cosmid T13F2, with the addition of SmaI and BamH1 sites to facilitate cloning the polynucleotide of interest: CCCGGGTGGATCCGGAACATATCACACGAAACAG; SEQ. ID NO: 8. This primer begins 93 base pairs after the putative stop codon TAG and ends 20 base pairs upstream of the predicted polyadenylation signal (AAUAAA; SEQ ID NO: 9) of the fat-4 gene.

For the determination of trans-splicing of specific leader sequences, downstream primers corresponding to the complement of bases 35009-35028 of the T13F2 (TCTGGGATCTCTGGTTCTTG; SEQ. ID NO: 10) were used for the T13F2.1 gene. The upstream PCR primers were either SL1-20 or SL2-20 (Spieth et al., *Cell* 73:521-532, 1993). The *C. elegans* homologue of the ribosomal-protein L37 was used as an SL1-specific control, and K06H7.3 was used as an SL2-specific control (Zorio et al., *Nature* 372: 270-272, 1994. SL1-20, SL2-20, and control primers were kindly provided by Diego A. R. Zorio. RT-PCR products visualized by gel electrophoresis were confirmed by blotting the gel and probing with gene-specific oligonucleotides corresponding to the appropriate gene as previously described (Spieth et al., *Cell* 73:21-532, 1993).

Example 4: PCR Amplification of the Genes Encoding $\Delta^5$ and $\Delta^8$ Desaturases DNA and protein sequences were analyzed using the Wisconsin-GCG package of programs (Devereux et al., *Nucleic Acids Res.* 12:387-95, 1984).

To clone the *E. gracilis* ($\Delta^8$) open reading frame as a single DNA fragment, a set of primers was used to prime a reverse transcription specifically for the open reading frame. The primer for the 5' end of the gene began 3 nucleotides before the start codon and included the first 26 nucleotides of the open reading frame. The 3' primer was complementary to the sequence between 22 and 52 nucleotides downstream from the predicted termination codon. This PCR amplification was conducted with Pfu polymerase to minimize the chance of an amplification error. The PCR reactions produced a single band of the predicted size when analyzed by agarose gel electrophoresis. This band was cloned into the vector pCR-Script Cam™ (Stratagene), and a single clone designated pJW541 was chosen for analysis.

The plasmid containing SEQ ID NO: 3, described herein as pJW541, was deposited in the American Type Culture Collection (10801 University Boulevard, Manassas, Va. 20110) on May 20, 2003 (ATCC Accession No. PTA-5206).

To express the *C. elegans* $\Delta^5$-desaturase, the fat-4 cDNA amplification product (see Example 3) was digested with HindIII and BamH1 and ligated to the yeast expression vector pYES2 (Invitrogen) cut with HindIII and BamH1. The resulting plasmid was named pYFAT4.

Example 5: Expression of $\Delta^5$ and $\Delta^8$-Desaturases

For *E. gracilis*, the cloned $\Delta^8$ gene was transferred to the yeast expression vector pYES2 (Invitrogen, Carlsbad, Calif.) by standard cloning techniques (Ausubel, *Current Protocols In Molecular Biology*, 1988) using enzymes obtained from New England Biolabs, Beverly, Mass. The resulting yeast expression construct containing the open reading frame under the control of a galactose-inducible promoter was designated pYES2-541.

*Saccharomyces cerevisiae* strain INVSc1 (Invitrogen) was transformed with pYES2-541 and cultured using standard methods (Ausubel, *Current Protocols In Molecular Biology*, 1988). Liquid medium containing 2% galactose was supplemented with fatty acid soaps (NuCheck Prep, Elysian Minn.) at a final concentration of 0.2 mM. Tergitol (1%, NP40) was added to the yeast cultures to enhance fatty acid uptake (Stukey et al., *J. Biol. Chem.* 264:16537-16544, 1989), except for cultures containing 20:1, where 5% DMSO was substituted. Yeast were incubated overnight at 28° C., harvested by centrifugation, washed once with 1% Tergitol, once with 0.5% Tergitol, and finally once with distilled water.

For the *C. elegans* $\Delta^5$ gene, the constructs were transformed into *Saccharomyces cerevisiae* strain INVSc1 using the S.c. EasyComp transformation kit (Invitrogen). For experiments with the FAT-4 peptide, transformed yeast were grown overnight in uracil-deficient media containing 2% galactose, 0.2 mM fatty acid, and 1% NP-40. Under these conditions the percentage of these supplemented fatty acids which were incorporated into yeast lipids ranged from 14-28% of the total yeast fatty acids. For experiments in which 20:1$\Delta^{11}$ was used as a substrate, the 1% NP-40 was replaced by 5% DMSO to achieve better incorporation of this fatty acid.

Example 6: Analysis of Fatty Acids Using Gas Chromatography and GC-Mass Spectrometry Extraction of lipids and preparation of fatty acid methyl esters was carried out by standard methods (Miguel and Browse, *J. Biol. Chem.* 267:1502-1509, 1992). Gas chromatography of the methyl esters was conducted by established methods (Spychalla et al., *Proc. Natl. Acad. Sci. USA* 94:1142-1147, 1997). Fatty acid 4,4-Dimethyloxazoline (DMOX) derivatives of yeast lipid extracts were prepared by standard methods (Fay and Richli, *J. Chromatogr.* 541:89-98, 1991). GC-mass spectrometry was conducted on a Hewlett-Packard 6890 series GC-MS fitted with a 30 m×0.25 µm HPSMS column, operating at an ionization voltage of 70 eV with a scan range of 50-550 Da. Fatty acids and their derivatives were identified where possible by comparison with authentic standards (NuCheck Prep).

Example 7: Identification and Amplification of the *Euglena* $\Delta^8$-Desaturase Gene Messenger RNA isolated from heterotrophic cultures was used as template for reverse transcription followed by PCR amplification using degenerate primers that spanned the first and third conserved histidine-rich regions of microsomal desaturase proteins. The *C. elegans* $\Delta^6$-desaturase gene, FAT-3, was used as the principal basis for primer design. To compensate for the high degeneracy necessary in the primer pair, amplification reactions began with five cycles of low-temperature annealing and a long temperature ramp between the annealing and polymerization steps. Preliminary amplifications to optimize thermal cycling parameters used the proofreading Pfu DNA polymerase. After successful Pfu amplification reactions using high primer and magnesium concentrations, Taq polymerase was used to generate a number of bands detectable on agarose gels.

Several of these bands, of approximately 650 bp, had identical sequence. This DNA sequence contained an open reading frame in which the predicted amino acid sequence was homologous to other membrane desaturases, and included a characteristic central His-box. Primers designed to be specific to the amplified sequence were used to amplify the termini of the cDNA using 3' and 5' RACE techniques. The full-length cDNA for this gene was 1745 bp in length. It included an open reading frame of 1272 bp and a 472-bp 3' untranslated region. Most *Euglena* messenger RNAs are processed through the addition of a short 5' RNA leader sequence, the trans-spliced leader (Tessier et al., *Embo. J.* 10:2621-2625, 1991). This RNA processing step left a conserved sequence (TTTTTTTCG; SEQ. ID NO. 11) at the beginning of each message (Cui et al., *J. Biochem.* (Tokyo) 115:98-107, 1994). The presence of this leader in the cDNA sequence confirmed that the message was full-length at the 5' end. RT-PCR with primers flanking the open reading frame on the 5' and 3' ends resulted in a single band that was cloned into the vector pCR-Script Cam™ (Stratagene), and designated pJW541. The gene corresponding to this ORF was designated EFD1 (*Euglena* fatty acid desaturase 1).

Example 8: Similarity Between *Euglena* $\Delta^8$-Desaturase and Other Proteins The translated open reading frame indicated a protein of 422 amino acids with a predicted molecular mass of 48.8 kDa. (FIG. 3). A BLAST™ search of sequence databases revealed that the predicted protein sequence exhibited regions of homology with the known group of membrane fatty acid desaturases, especially in the highly conserved histidine-rich regions (Shanklin et al., *Biochemistry* 33:12787-12794, 1994).

Each of the His-box motifs is present in the EFD1 protein. The first (HXXXH; SEQ ID NO: 17) starts at amino acid 146 and the second (HXXHH; SEQ ID NO: 12) at amino acid 183 (FIG. 3). EFD1 contains a variant third His-box, QXXHH (SEQ ID NO: 13), starting at amino acid 361, similar to the cloned $\Delta^5$- and $\Delta^6$-desaturases. EFD1 exhibits conservation of protein sequence in the regions surrounding the highly conserved regions, especially with FAT-3 and FAT-4, the $\Delta^6$- and $\Delta^5$-desaturases of *C. elegans* (FIG. 3). Outside the highly conserved regions, the amino acid sequence shows considerably less similarity to other desaturases. Overall, the amino acid identity with FAT-3 and FAT-4 is 33%, compared to 28% identity with the borage $\Delta^6$-desaturase.

EFD1 also contains a cytochrome $b_5$-like motif at its N-terminus. The protein encodes seven of the eight most highly conserved amino acids characteristic of cytochrome $b_5$ (FIG. 3), which are responsible for heme binding. Similar motifs are found at the N-terminal regions of FAT-3 and FAT-4 (FIG. 3), and the borage $\Delta^6$ protein, as well as the carboxyl terminus of a yeast $\Delta^9$ protein.

The structure of the *Euglena* protein also exhibits similarities with known desaturases. Membrane desaturases are type II multiple membrane spanning proteins, and hydropathy analysis of the cloned *Euglena* gene indicates that the predicted protein has at least three significant hydrophobic regions long enough to span the membrane bilayer twice. As is true for most desaturase enzymes, there are 31 amino acid residues between the first two His-boxes. The distance between the between the second and third His-box is 173 residues, within the range previously observed (Shanklin and Cahoon, *Annu. Rev. Plant Physiol. Plant Mol. Biol.* 48:611-641, 1998).

Example 9: Activity of the *Euglena* $\Delta^8$-Desaturase Protein

To confirm the activity of the enzyme, the EFD1 cDNA was transferred from pJW541 to yeast expression vector pYES2 under the control of a galactose-inducible promoter. The resulting construct, pYES2-541, was introduced into *S. cerevisiae*. Yeast membranes do not contain 20-carbon fatty acids but incorporate them from the culture medium. Accordingly, yeast cultures were supplemented with various fatty acid soaps, using a yeast strain containing the empty vector as control, and analyzed the fatty acids of the cultures by methyl-ester derivatization and gas chromatography.

Figure 4:
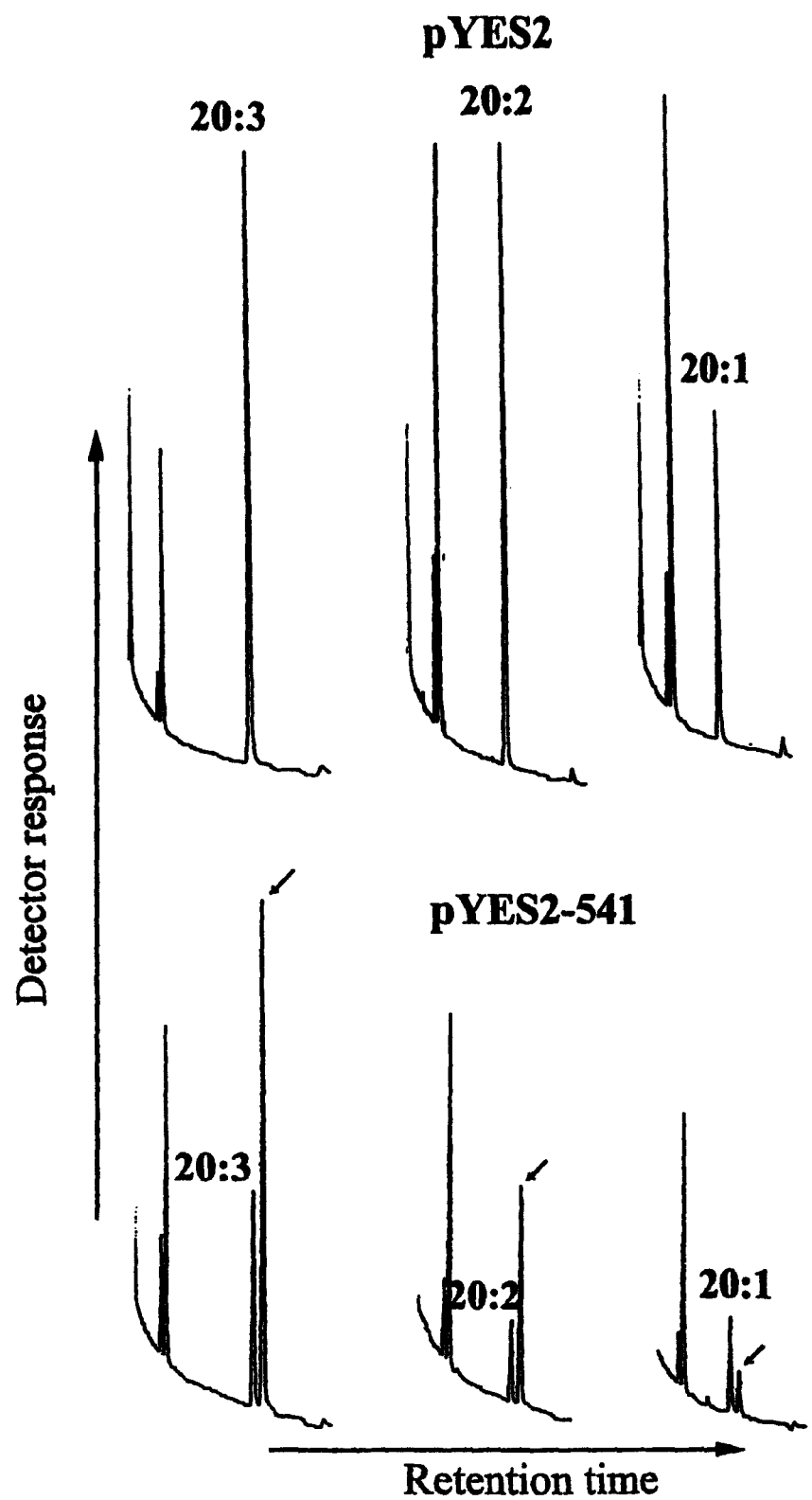
FIG. 4 shows the results of gas chromatography of fatty acid methyl esters from recombinant yeast. Cultures of yeast containing either control pYES2 or pYES2-541, which expresses the *Euglena* $\Delta^8$-desaturase (EFD1) gene, were supplemented with the indicated 20-carbon fatty acids. The control strain does not desaturate the exogenous fatty acids. For the experimental strain, an arrow indicates the desaturation peak.

The patterns of desaturation activity in these experiments indicated that pYES2-541 expresses a $\Delta^8$-desaturase enzyme that does not have $\Delta^5$ or $\Delta^6$ activity. The ability of the experimental yeast strain to produce $\Delta^8$ desaturation was shown when the culture medium was supplemented with 20:2 (FIG. 4). A desaturation peak whose retention time is identical to authentic 20:3 was produced. The vector-only control culture did not desaturate 20:2 (FIG. 4). The yeast strain expressing the *Euglena* gene also desaturated 20:3 and 20:1 (FIG. 4), again without desaturation activity in the control cultures. The cloned *Euglena* protein was most active with 20:3 and 20:2 as substrates, desaturating 70% and 73% of the total incorporated 20-carbon fatty acid. EFD1 was least active with 20:1, converting 32% of that substrate to a desaturation product (FIG. 4).

When the culture medium was supplemented with a substrate for $\Delta^5$-desaturation, 20:4, the fatty acid was incorporated into the yeast, but no 20:5 desaturation product was produced. Similarly, when the medium was supplemented with 18:2 and 18:3, no desaturation occurred, demonstrating that the cloned gene did not express a $\Delta^6$-desaturase.

Figure 5A:
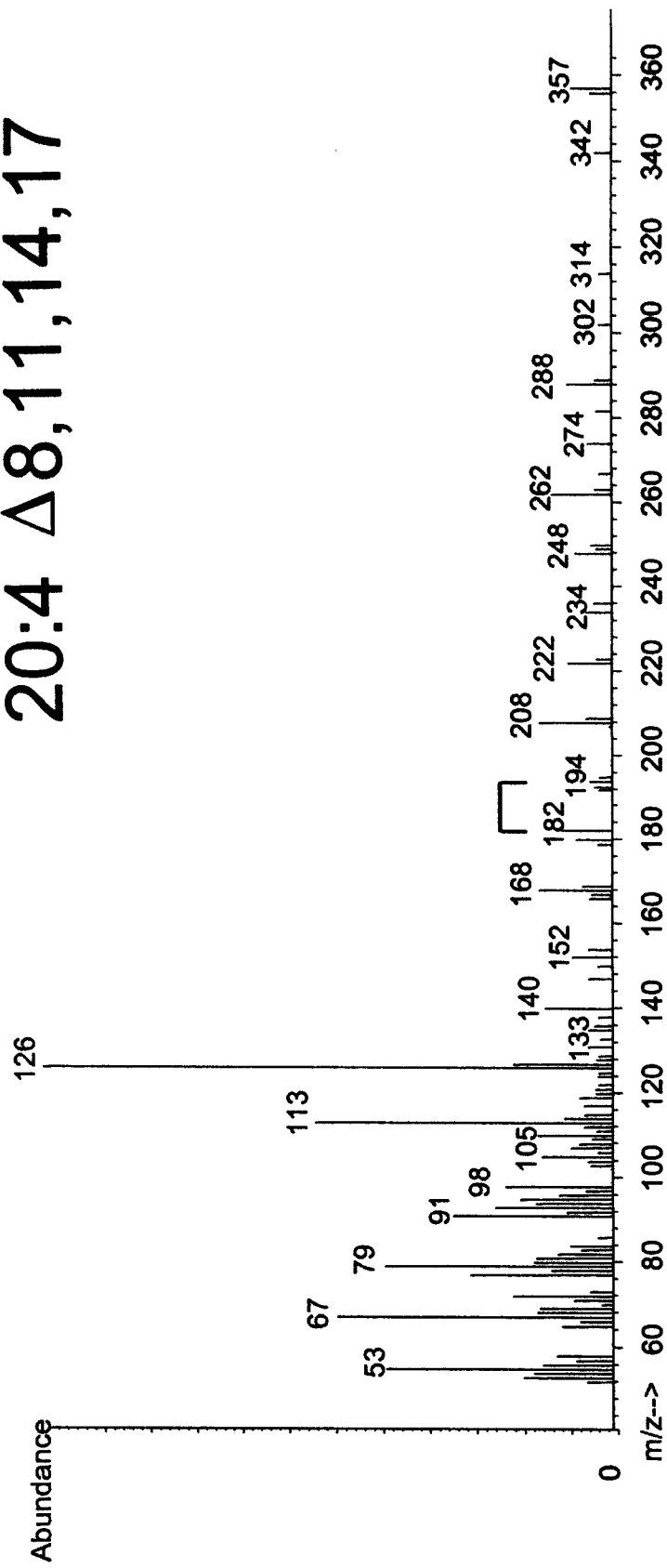
FIGS. 5A-5C show the results of mass spectrometry (MS) of desaturation products. DMOX derivatives of EFD1 desaturation products were analyzed by GC-mass spectrometry. The molecular ion of each fatty acid is 2 a.m.u. (atomic mass units) less than the substrate provided, as expected for insertion of a double bond. Desaturation at the $\Delta^8$ position is established by characteristic m/z peaks of 182 and 194 for each product, indicated by the bracket.
Figure 5B:
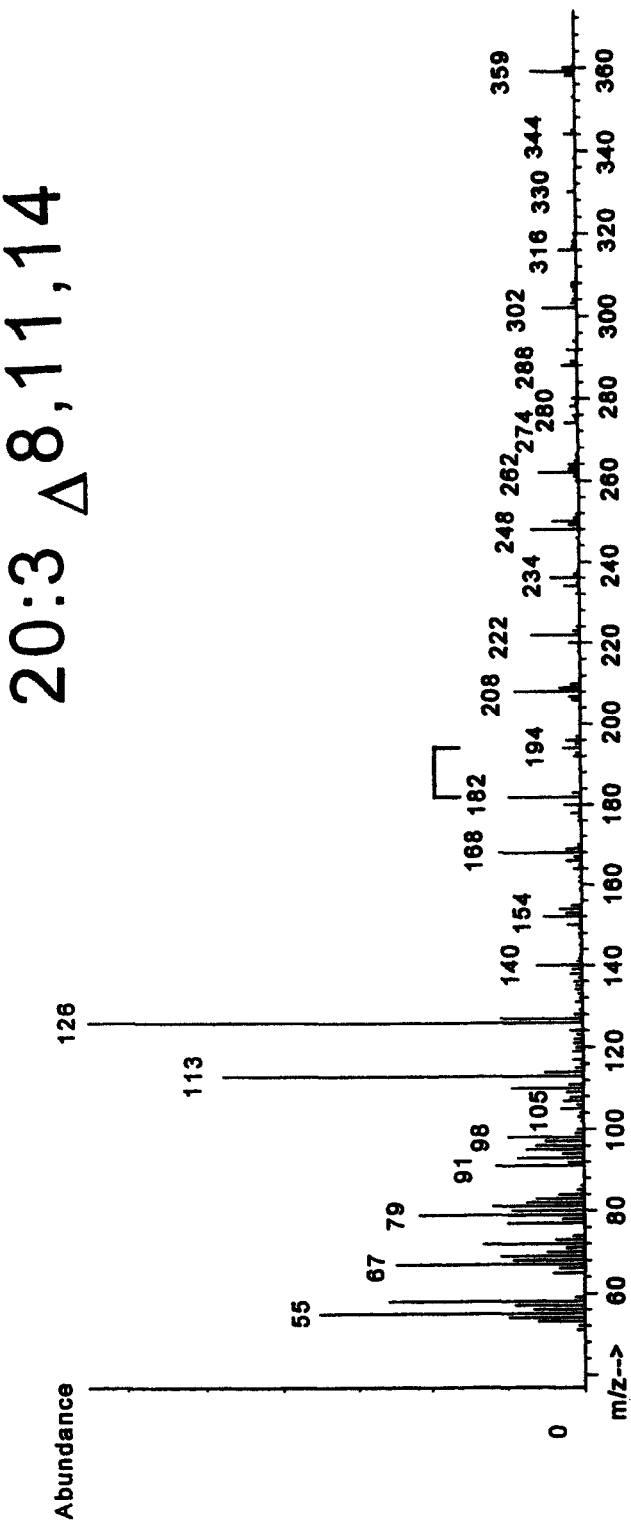
Figure 5C:
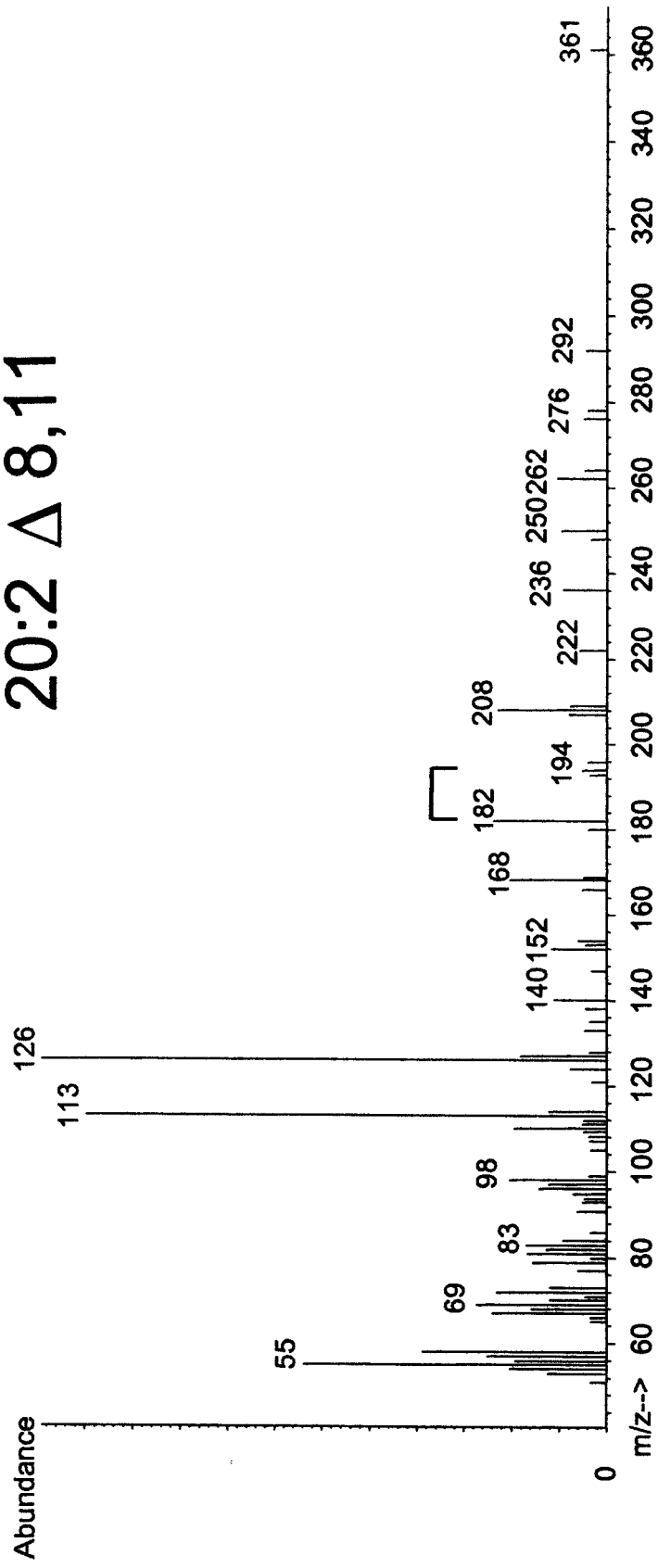

To confirm that desaturation had occurred at the $\Delta^8$ position, 4,4-dimethyloxazoline (DMOX) derivatives of yeast fatty acids were analyzed by GC-MS. DMOX derivatives have mass spectra that are more easily interpreted than spectra of methyl esters, and permit unambiguous determination of double-bond locations in polyunsaturated fatty acids (Christie, *Lipids* 33:343-353, 1998). For the experiment that desaturated the fatty acid 20:2, the retention time of the product on the GC-MS instrument was 16.8 min., identical to DMOX-derivatized authentic 20:3. The mass spectrum of this desaturation product and its molecular ion (m/z 359) indicated that it was the 20:3 compound. Two spectral frequency peaks at m/z 182 and 194, separated by only 12 a.m.u., showed that the introduced double bond was at the $\Delta^8$ position (FIG. 5). (The substrate 20:2, which is saturated at the 8-position, has peaks at 182 and 196, separated by 14 a.m.u.) The spectrum of the product, with its desaturation peaks, was identical to that of authentic 20:3 (Luthria and Sprecher, *Lipids* 28:561-564, 1993). The other substrates, 20:1 and 20:3, were also desaturated at the $\Delta^8$-position by EFD1. The peaks at m/z 182 and m/z 194 appeared in the spectrum of each, and the molecular ion was reduced from that of the substrate by two in each case (FIGS. 5A-5C).

Figure 8:
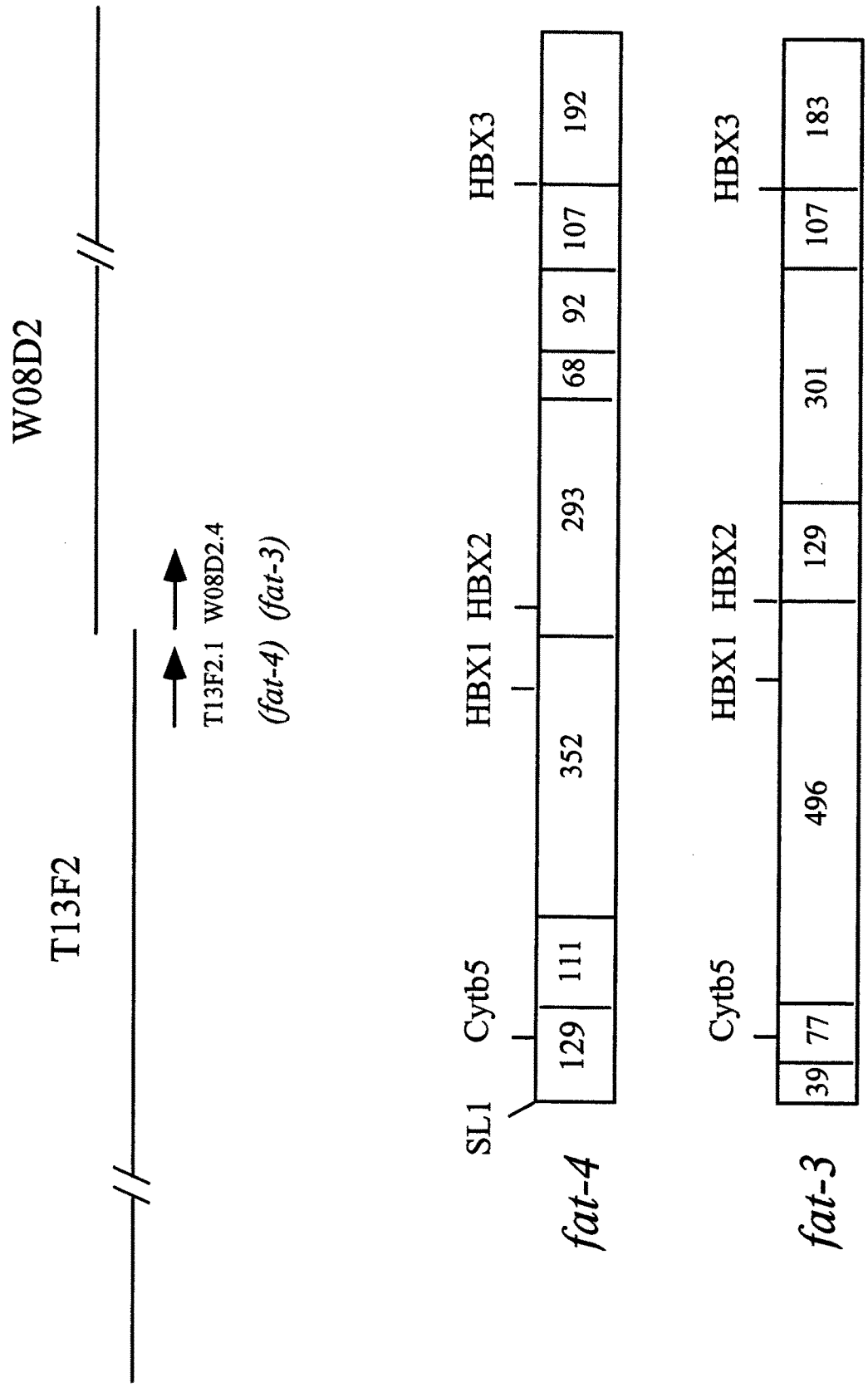
FIG. 8 shows certain features of the structure of the *C. elegans* $\Delta^5$- and $\Delta^6$-desaturase genes. The relative location of gene products T13F2.1 and W08D2.4 on their respective cosmids is shown above. The exon structure of T13F2.1 (fat-4) and W08D2.4 (fat-3) showing the sites of sequences encoding the SL1 splice site, the heme-binding motif of cytochrome $b_5$ (cyt $b_5$), and the three conserved histidine box motifs (HBX) is shown below.

Example 10: Identification and Cloning of Two Fatty Acid *C. elegans* Desaturase Genes Two high-scoring open reading frames were identified during a search of the *C. elegans* genomic DNA database with the borage $\Delta^6$-desaturase protein sequence. Both proteins predicted from these open reading frames, W08D2.4 and T13F2.1, contained an N-terminal sequence resembling cytochrome $b_5$, including the characteristic (HPGG) heme binding domain, and an H→Q substitution in the third histidine box. The W08D2.4 gene was denoted fat-3 and the T13F2.1 gene was denoted fat-4, since they both appear to encode fatty acid desaturases. Interestingly, the fat-3 and fat-4 genes are located next to each other on overlapping cosmids in the same 5' to 3' orientation, with only 858 nucleotide base pairs separating the putative polyadenylation signal of the fat-4 gene and the ATG start codon of the fat-3 gene (FIG. 8). This gene organization is reminiscent of operons, in which two or more genes are transcribed under the control of a single promoter and regulatory region.

In *C. elegans* the polycistronic pre-mRNA is converted to monocistronic mRNA by cleavage and polyadenylation at the 3' end of the upstream gene and transplicing to the SL2 sequence at the 5' end of the downstream gene, with the two mRNAs being subsequently independently translated. However, out of more than 30 such operons that have been analyzed, the distances between the 3' end of the upstream gene and the 5' end of the downstream gene are generally about 100 base pairs, with a few separated by 300-400 base pairs (Blumenthal et al, *C. elegans* II, pp. 117-145, Cold Spring Harbor Laboratory Press, Cold Spring, N Y, 1997).

The *C. elegans* fat-3 and fat-4 genes were tested to determine whether they were trans-spliced to either SL1 or SL2 in order to determine if they might be co-transcribed in a single operon. It was found that the fat-4 gene was transpliced to SL1, but that the fat-3 gene was not transpliced to either spliced leader sequence. Therefore, it was concluded that each gene contains its own 5' promoter and regulatory region.

Both of these genes were cloned using RT-PCR. The fat-4 gene sequence matched the T13F2 genomic sequence exactly. However the gene product encoded by the cDNA was seven amino acids shorter than predicted by Genefinder for T13F2.1 (GenBank accession number Z81122) because the DNA sequence encoding amino acid residues 198-204 was not present in the fat-4 cDNA. The resulting peptide length was 447 amino acids instead of the previously predicted 454 amino acids. The gene product encoded by the fat-3 cDNA also matched the genomic sequence of W08D2.4 (GenBank accession number Z70271) perfectly. However, the gene product was also shorter than the predicted protein sequence. Codons for amino acid residues 38-67 of W08D2.4 were not present in the cDNA. In both cases the gene-prediction software used in the genomic sequencing project appeared to have misidentified some intron DNA as coding sequences.

Example 11: Sequence Comparisons for *C. elegans* $\Delta^5$

The *C. elegans* FAT-3 and FAT-4 proteins, the *Mortierella alpina* $\Delta^5$-desaturase, and the *B. officinalis* $\Delta^6$-desaturase appear to be proteins of similar structure in that they all contain an N-terminal cytochrome $b_5$ domain, three histidine boxes, and distinct hydrophobic membrane-spanning domains predicted by the TMHMM program from the Center for Biological Sequence Analysis, Technical University of Denmark (http://www.cbs.dtu.dk/services/TMHMM-1.0/). The predicted structure is consistent with the proposed desaturase structural model (Stukey et al., *J. Biol. Chem.,* 265:20144-20149, 1990). Despite these similarities, the overall sequence identity among the four proteins is quite low. For example, the FAT-3 $\Delta^6$-desaturase and the borage $\Delta^6$-desaturase share only 28% identity on the amino acid level. The fat-4 gene product shares 25% amino acid identity with the borage $\Delta^6$-desaturase and 19% amino acid identity with the *Mortierella alpina* $\Delta^5$-desaturase. Indeed the only portion of the FAT-4 protein that shows extended homology to the *M. alpina* $\Delta^5$-desaturase is a sequence of 36 residues incorporating the third His box which has 44% identity and 56% similarity. The most closely related pair of sequences are fat-3 and fat-4, which are 46% identical on the amino acid level and 54% identical over the entire cDNA sequence.

Figure 9:
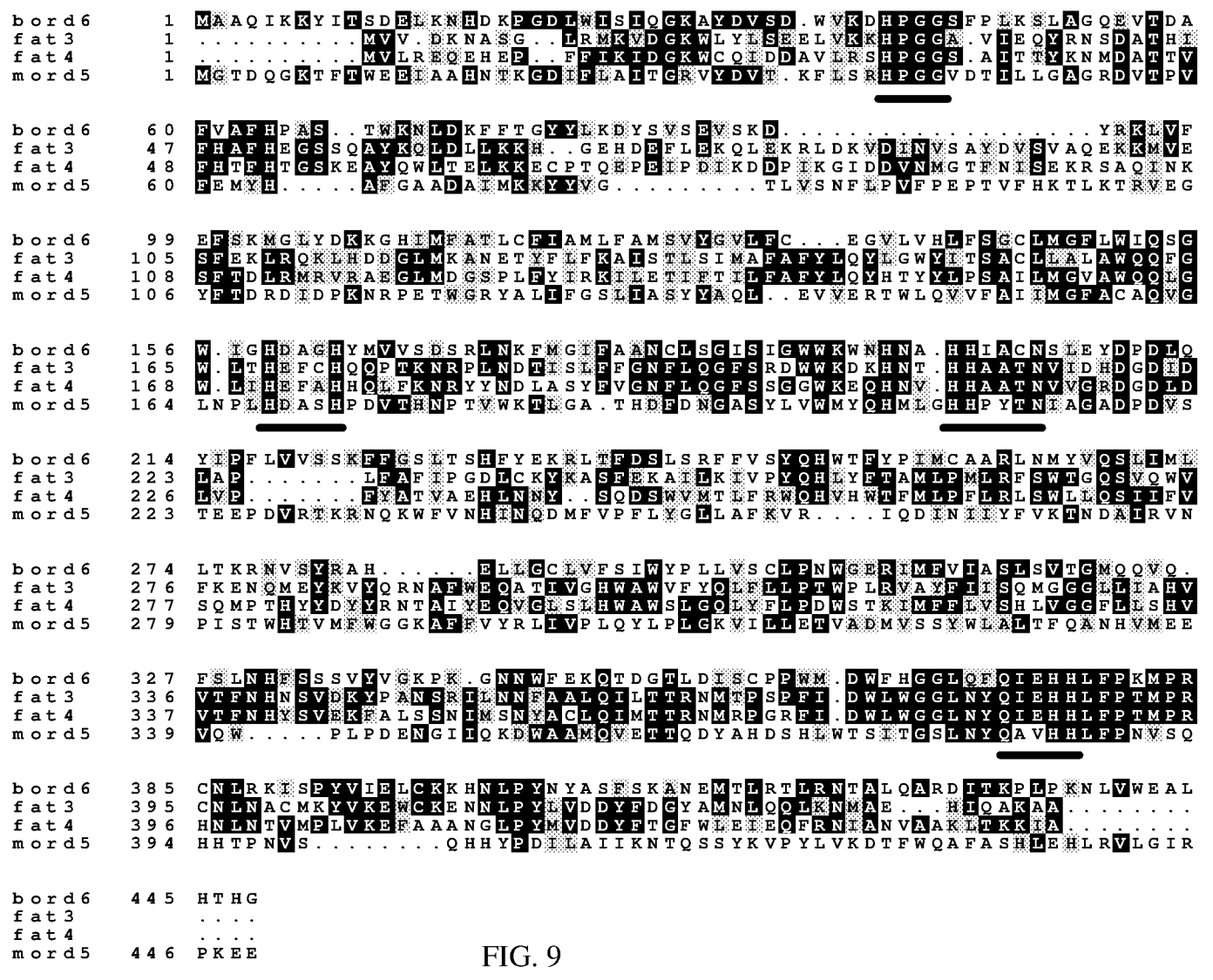

FIG. 9 shows the sequence comparison of the borage $\Delta^6$-desaturase, *C. elegans* FAT-3, *C. elegans* FAT-4, and the *Mortierella alpina* $\Delta^5$-desaturase. The similar heme-binding domains (HPGG) and the three histidine box regions are underlined. The presence of these conserved motifs indicate that the fat-4 gene may encode a desaturase or a related fatty acid modifying enzyme. However it is not possible, from these sequence comparisons alone, to predict whether this gene encodes a $\Delta^6$-desaturase, a $\Delta^5$-desaturase, or a more distantly related enzyme.

Figure 10A:
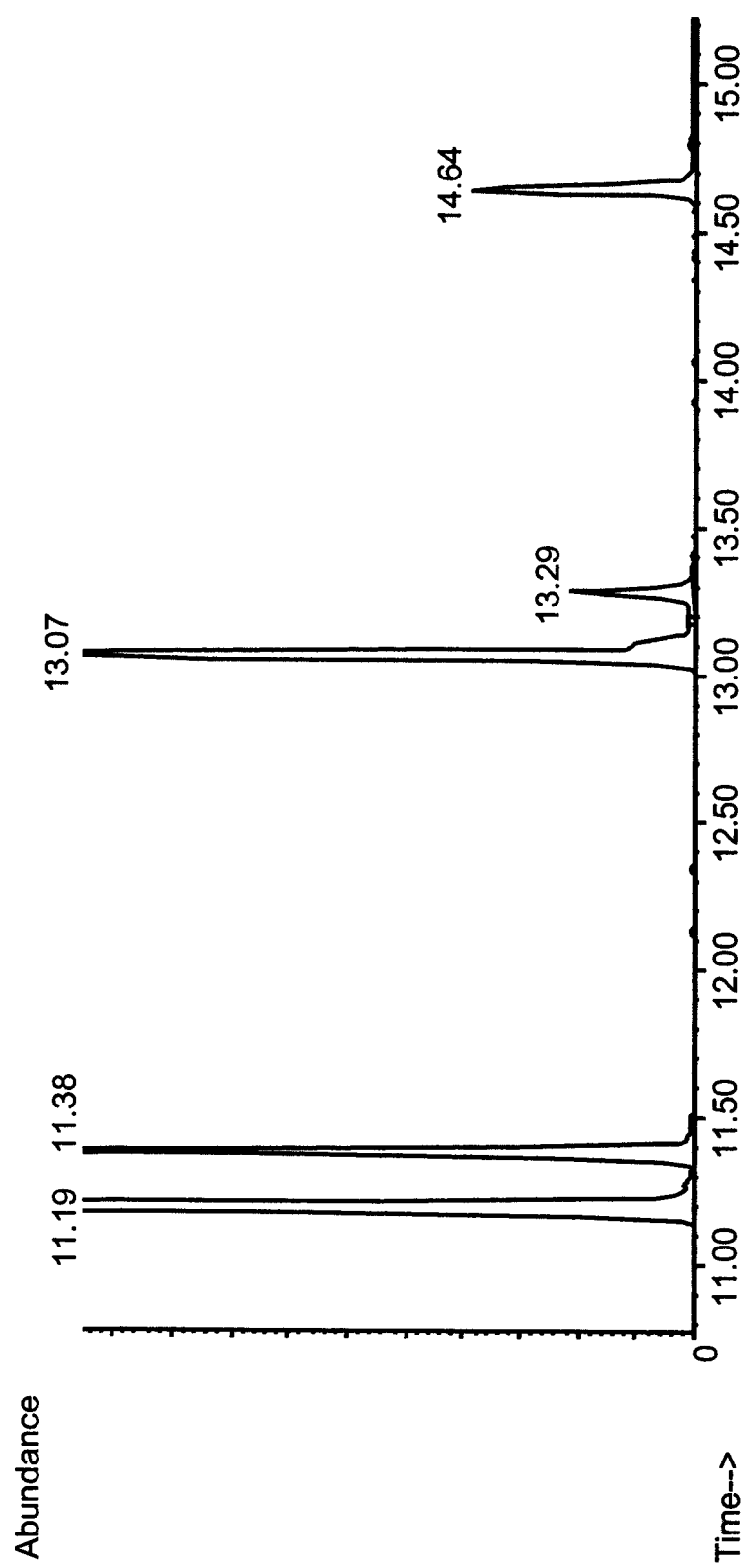
FIGS. 10A-10C show identification of arachidonic acid in transgenic yeast by gas chromatography-mass spectroscopy (GC-MS). Fatty acid methyl esters of total lipids of *S. cerevisiae* grown for 16 hours under inducing conditions (2% galactose) supplemented with 0.2 mM di-homo-γ-linolenic acid were analyzed by GC-MS. (A) Yeast transformed with (empty) vector pYES2. (B) Yeast transformed with pYES2 vector carrying fat-4. The common peaks were identified as 16:0 (11.19-11.12 min.), 16:1 (11.38 min.), 18:0 (13.07-13.08 min.), 18:1 (13.29 min.), 20:3 (11.64-11.65 min.). The novel peaks are arachidonic acid (14.49 min.) and 18:2 (12.91 min.). (C) The mass spectrum of the peak eluting at 14.49 min. This spectrum is indistinguishable from that of authentic methyl-arachidonate.
Figure 10B:
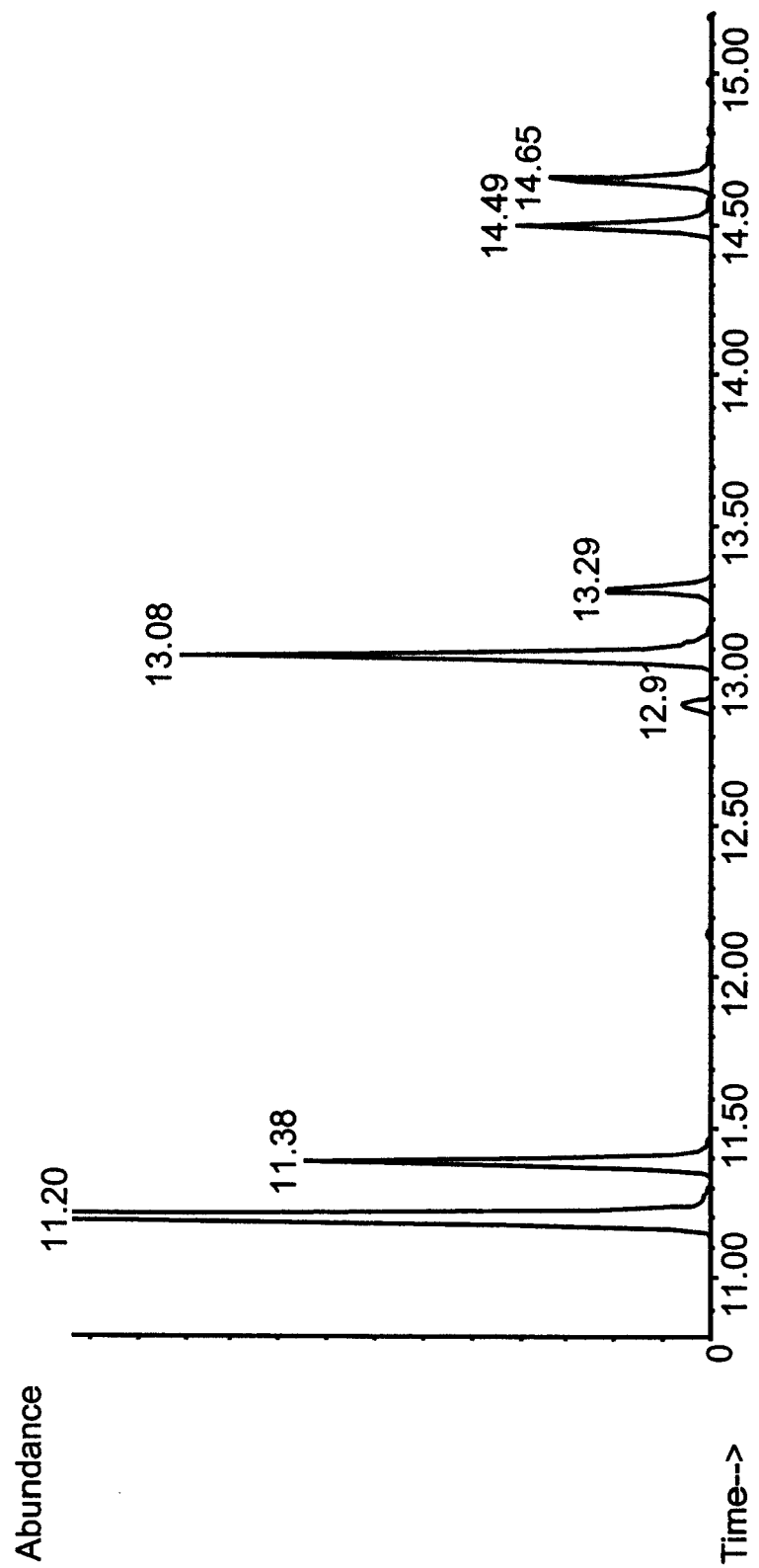
Figure 10C:
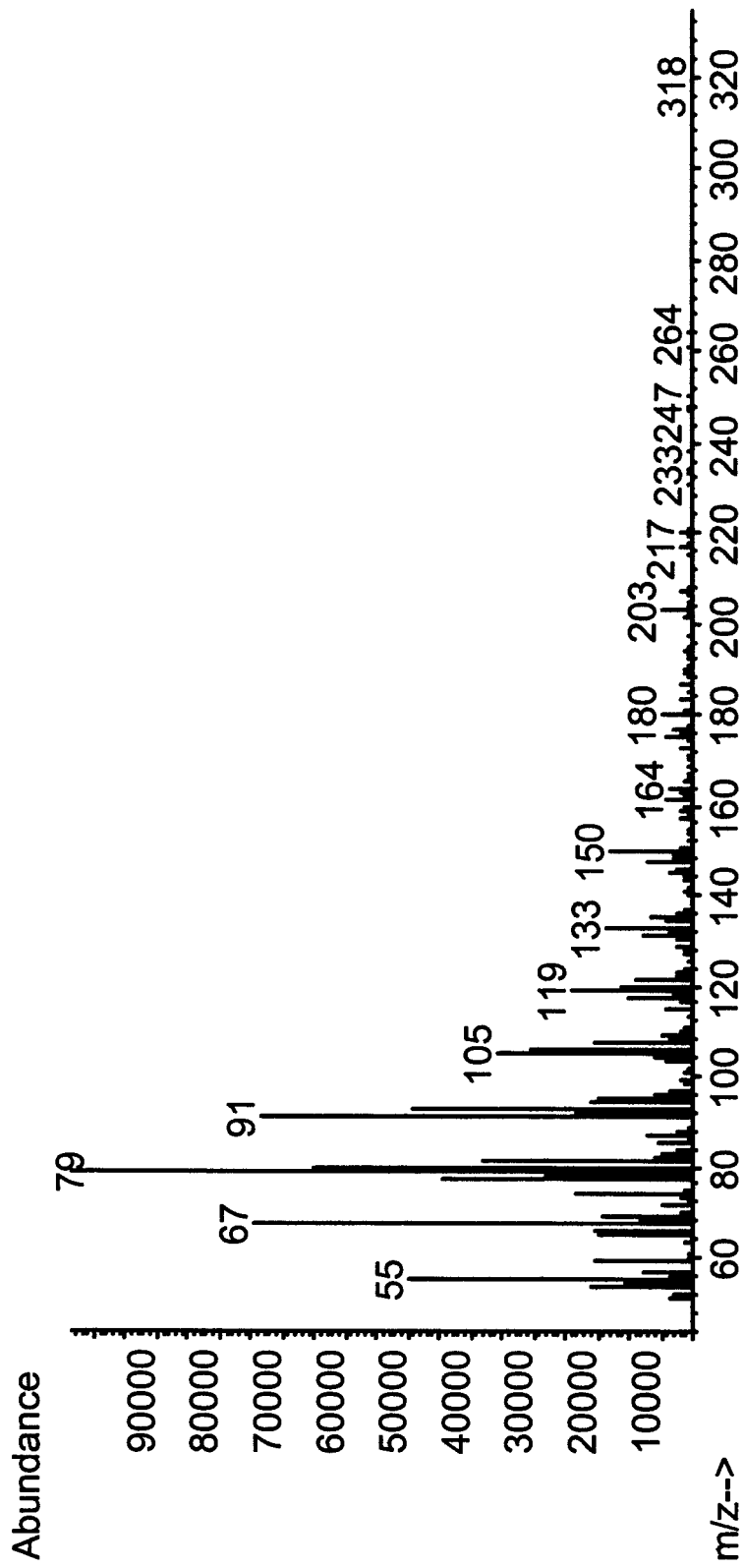

Example 12: Fatty Acid Desaturase Activity and Substrate Specificity in Yeast for *C. elegans* $\Delta^5$ To determine the enzymatic activity of the FAT-4 desaturase-like protein, the protein was expressed in *Saccharomyces cerevisiae* supplemented with polyunsaturated fatty acid substrates that are not normally present in this yeast. The FAT-4 protein was expressed in the yeast expression vector pYES2 from the GAL1 promoter by growing the cells in the presence of galactose and various fatty acids. After 16 hours of growth, the cells were analyzed for total fatty acid composition by gas chromatography (GC). Comparison of cells supplemented with di-homo-γ-linolenic acid ($20:3\Delta^{8,11,14}$) carrying pYES2 containing the fat-4 coding sequence and cells carrying the vector alone revealed the presence of a major new peak eluting at 14.49 minutes in the cells expressing FAT-4 (FIG. 10B). The novel peak had a retention time identical to that of the authentic arachidonic acid methyl ester ($20:4\Delta^{5,8,11,14}$), and was determined to be arachidonic acid ($20:4\Delta^{5,8,11,14}$) because its mass spectrum was identical to that of authentic arachidonic acid methyl ester, including a mass ion peak at m/z 318.

The identity of this compound was further verified by converting the yeast fatty acid methyl esters into oxazoline derivatives in order to produce structure specific mass spectra which simplify the determination of double-bond positions in a hydrocarbon chain. The mass spectrum of the DMOX derivative of the novel 20:4 component was consistent with the published spectrum for arachadonic acid and contained a prominent peak at m/z 153, which is diagnostic of a double bond at the $\Delta^5$ position. Therefore, it was concluded that the fat-4 gene encodes a $\Delta^5$-desaturase capable of synthesizing arachidonic acid from the substrate di-homo-γ-linolenic acid. In contrast, the FAT-4 protein showed no activity when linoleic acid (18:2$\Delta^{9,12}$) or γ-linolenic acid (18:3$\Delta^{9,12,15}$) were provided as substrates, indicating an absence of $\Delta^6$-desaturase activity.

Further analysis of the GC trace of the total fatty acids of the yeast cells expressing fat-4 revealed the presence of a second novel peak eluting at 12.91 minutes which was not present in the empty vector control cells. Analysis of the mass spectrum of this novel peak revealed a molecular ion species of 294, identical to that of a methyl ester of an 18-carbon fatty acid with two double bonds (18:2), but its retention time and mass spectrum were not identical to the common isomer 18:2 $\Delta^{9,12}$.

In microsomal extracts of mammalian liver, $\Delta^5$-desaturase activity has been reported to act on a number of 18 and 20-carbon precursors to produce uncommon fatty acids such as 18:2$\Delta^{5,11}$, 20:3$\Delta^{5,11,14}$ and 20:4$\Delta^{5,11,14,17}$ (28, 29). Two species of slime molds have also been reported to produce small amounts of 18:2$\Delta^{5,9}$, 18:2$\Delta^{5,11}$, 20:3$\Delta^{5,11,14}$ and 20:4$\Delta^{5,11,14,17}$ (Rezanka, *Phytochemistry*, 33:1441-1444, 1993). These fatty acids are unusual in that their double bonds do not follow the conventional methylene-interrupted pattern (one double bond every three carbons).

Therefore, it was suspected that the novel peak exhibited on the GC spectrum is a result of the *C. elegans* $\Delta^5$-desaturase acting on 18:1$\Delta^9$ (or 18:1$\Delta^{11}$, which in *S. cerevisiae* constitutes 15-20% of the total 18:1) compound, to produce the uncommon isomer 18:2$\Delta^{5,9}$ or 18:2$\Delta^{5,11}$. These yeast fatty acid methyl esters were converted into oxazoline derivatives. It was found that the mass spectrum of the DMOX derivative of the novel 18:2 component contained the $\Delta^5$-specific peak at m/z 153. However the larger ion peaks characteristic of double bonds at the $\Delta^9$ or $\Delta^{11}$ position were not detected due to the small amount of this molecule present in the total yeast extracts.

To test if the *C. elegans* $\Delta^5$-desaturase was capable of desaturating other substrates to produce other uncommon, non-methylene-interrupted fatty acids, the yeast expressing the FAT-4-desaturase was supplemented with unconventional $\Delta^5$-substrates, such as 20:1$\Delta^{11}$, 20:2$\Delta^{11,14}$ and 20:3$\Delta^{11,14,17}$. No novel peaks were detected when the substrate 20:1$\Delta^{11}$ was fed to yeast. However, when 20:2$\Delta^{11,14}$ and 20:3$\Delta^{11,14,17}$ were provided as substrates, novel peaks were detected eluting at 14.62 minutes and 14.69 minutes, respectively (FIGS. 11A and 11B, respectively). The mass-spectrum analysis of DMOX derivatives of these molecules yielded results consistent with published values for 20:3$\Delta^{5,11,14}$ and 20:4$\Delta^{5,11,14,17}$, including a prominent ion peak of m/z 153 (which is diagnostic of double bonds at the $\Delta^5$ position). It was found, however, that these fatty acids were not produced to the same extent as arachidonic acid (20:4$\Delta^{5,8,11,14}$) (FIG. 12). In these experiments, 55% of exogenously fed di-homo-γ-linolenic acid (20:3$\Delta^{8,11,14}$) was converted to arachidonic acid, while only 5%, 27%, and 26% of the 18:1, 20:3$\Delta^{11,14}$, and 20:2$\Delta^{11,14,17}$ substrates were converted (FIG. 12).

The fat-3 gene was expressed in the yeast expression vector pMK195 containing the constitutive ADH promoter. The FAT-3 protein was able to desaturate linoleic acid (18:2$\Delta^{9,12}$) into γ-linolenic acid (18:3$\Delta^{6,9,12}$), in agreement with published results (Napier et al., *Biochem. J.* 330:611-614, 1998). It was also found that FAT-3 was capable of desaturating α-linolenic acid (18:3$\Delta^{9,12,15}$) to 18:4$\Delta^{6,9,12,15}$, a common reaction in animals. The FAT-3 protein showed no activity on 20:1$\Delta^{11}$, 20:2$\Delta^{11,14}$, 20:3$\Delta^{8,11,14}$, or 20:3$\Delta^{11,14,17}$. Therefore, the substrate specificities of the *C. elegans* $\Delta^5$ and $\Delta^6$-desaturases were determined to be specific and non-overlapping.

Example 13: Discussion of the *E. gracilis* $\Delta^8$-Desaturase

Desaturation at the $\Delta^8$-position has not been reported for any previously cloned gene (Tocher et al., *Prog. Lipid Res.* 37:73-117, 1998).

The predicted EFD1 protein has 33% amino acid identity with both FAT-3 and FAT-4, (FIG. 9), while its identity with the cloned borage $\Delta^6$-desaturase is 28%. The highest sequence conservation is found in the His-box motifs which are critical for desaturase activity, most likely because they serve as the diiron-oxo component of the active site (Shanklin et al., *Biochemistry* 33:12787-12794, 1994). Sequence conservation is also evident in the N-terminal cytochrome $b_5$-like domain, where most of the essential residues of cytochrome $b_5$ (Lederer, *Biochimie* 76:674-692, 1994) that are retained in FAT-3 and FAT-4 are also present in the EFD1 protein (FIG. 3).

Expression of the EFD1 gene in yeast was used to characterize its activity. Three different 20-carbon substrates with double bonds at the $\Delta^{11}$-position were desaturated (FIG. 4), and analysis of the products indicated that, for each one, desaturation had taken place at the $\Delta^8$ position (FIG. 5). The cloned *Euglena* desaturase showed a clear preference for the substrates of metabolic significance with greater than two-fold preference for 20:2 and 20:3 over 20:1 (Ulsamer et al., *J. Cell Biol.* 43:105-114, 1969). Even though EFD1 is quite similar to other microsomal desaturases, its activity was specific, as evidenced by its inactivity on substrates for $\Delta^5$ and $\Delta^6$ desaturation (FIG. 12).

Figure 2:
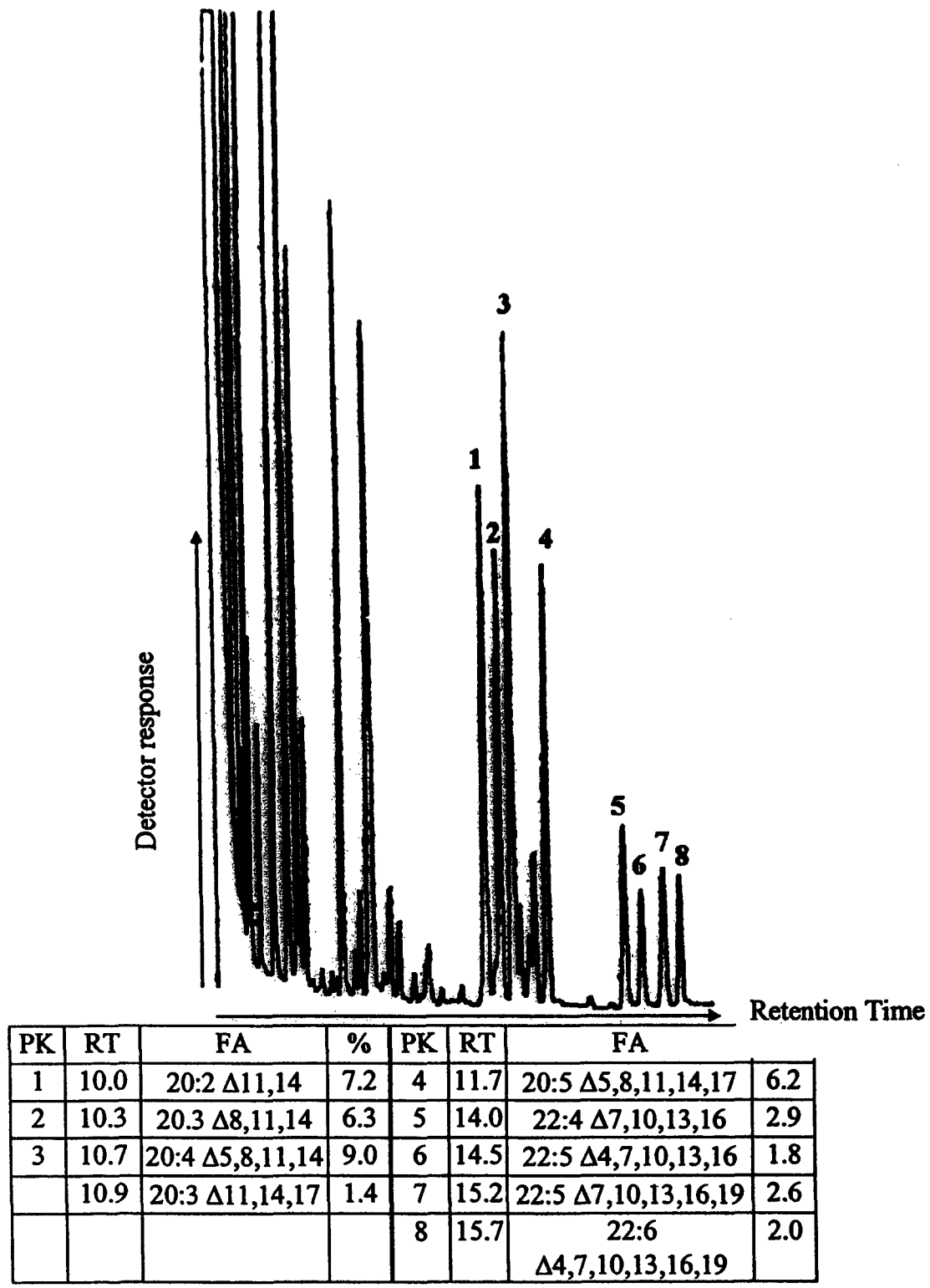
FIG. 2 shows gas chromatographic (GC) analysis of fatty acid methyl esters from *E. gracilis* grown (heterotrophically) in the dark with sucrose as carbon source. Fatty acids were identified by comparison of retention times with known standards. Significant peaks are numbered with their retention times and proportion of the total fatty acid indicated.

The 20-carbon substrates for $\Delta^8$ desaturation are available in abundance in heterotrophically grown *E. gracilis* (FIG. 2). These same substrates also are available in mammals, since 20:2 and 20:3 are produced by elongation from 18:2 and 18:3, in competition with the typical $\Delta^6$ desaturation (FIG. 1). Labeling experiments with rat liver homogenates indicate that elongation of the 18-carbon fatty acids is five-fold more rapid than the competing desaturation (Pawlosky et al., *J. Lipid Res.* 33:1711-1717, 1992).

Implicit in the current understanding of the $\Delta^6$ pathway of 20-carbon polyunsaturated fatty acid biosynthesis is a reliance on alternating desaturation and elongation to control flux through the pathway. While elongation often appears to be non-specific, most desaturations are specific both as to chain length of the substrate and to existing desaturation pattern of the fatty acid (Heinz, *Lipid Metabolism in Plants*, pp. 33-89, 1993). However, data from experiments in mammalian tissue (Bernert and Sprecher, *Biochim. Biophys. Acta.* 398:354-363, 1975; Albert et al., *Lipids* 14:498-500, 1979) and with yeast expressing the *C. elegans* $\Delta^5$-desaturase gene (FIG. 12), indicate that $\Delta^5$ enzymes desaturate fatty acids having a double bond at the $\Delta^{11}$-position but not at the $\Delta^8$-position, producing the non-methylene-interrupted 20:3 and 20:4 compounds at significant rates. For the $\Delta^8$ pathway, $\Delta^8$ desaturation occurs in competition with $\Delta^5$ activity on the substrates 20:2 and 20:3. In spite of this promiscuity of $\Delta^5$ enzymes, lipid profiles of mammalian tissue do not contain fatty acids with the $\Delta^{5,11}$ (Heinz, *Lipid Metabolism in Plants*, pp. 33-89, 1993; and Ulsamer et al., *J. Cell Biol.* 43:105-114, 1969) desaturation pattern, nor are they seen in *Euglena*.

One explanation may be that $\Delta^8$-desaturation of the common substrates occurs very rapidly, while $\Delta^5$-desaturation proceeds more slowly, so that little $\Delta^{5,11}$ product is formed. In support of this explanation, the *Euglena* $\Delta^8$ appears to be a very active desaturase when expressed in yeast (FIG. 4), compared to similarly expressed $\Delta^5$-desaturase enzymes. The *Euglena* desaturase must be sufficiently active to account for all the long chain polyunsaturates of rapidly growing *Euglena* cultures (FIG. 2). In contrast, the observed rates of $\Delta^8$-desaturation in mammalian tissue are relatively slow. The highest apparent rate occurs in cancerous tissues without $\Delta^6$ activity, where $\Delta^8$ desaturation permits production of arachidonic acid at only 17% of the level of comparable normal cells with $\Delta^6$ activity (Grammatikos et al., *Br. J. Cancer* 70:219-227, 1994).

Alternatively, the lack of $\Delta^{5,11}$ unsaturated fatty acids in membranes could be explained if the $\Delta^8$ desaturase accepts these fatty acids for desaturation. The convention that $\Delta^8$-desaturation precedes $\Delta^5$ activity (FIG. 1) is based on observations of desaturation reactions proceeding sequentially along the fatty acid hydrocarbon chain. The reverse order of desaturation, with $\Delta^5$-saturation preceding $\Delta^8$-desaturation, has been claimed (Takagi, *J. Chem. Bull. Japan* 38:2055-2057, 1965) and rejected (Schlenk et al., *Lipids* 5:575-577, 1970) in mammalian liver, and proposed as a likely pathway based on experiments with deuterated substrates in glioma cells (Cook et al., *J. Lipid Res.* 32:1265-1273, 1991).

In *Euglena* the products of $\Delta^8$-desaturation, $20:3\Delta^{8,11,14}$ and $20:4\Delta^{8,11,14,17}$ may be incorporated directly into membranes, or subjected to desaturation at the $\Delta^5$-position to produce arachidonic and eicosapentaenoic acids (Hulanicka et al., *J. Biol. Chem.* 239:2778-2787, 1964). Further elongation and desaturation leads to several polyunsaturated 22-carbon fatty acids (FIG. 2). In mammals, whether the products are derived from $\Delta^8$ or $\Delta^6$ activity, similar processes produce mostly arachidonic, eicosapentaenoic, and docosahexaenoic acid (22:6) (Hwang, *Fatty Acids in Foods and Their Health Implications*, pp. 545-557, 1992; Bernert and Sprecher, *Biochim. Biophys. Acta* 398:354-363, 1975; Lees and Korn, *Biochemistry* 5:1475-1481, 1966; Albert and Coniglio, *Biochim. Biophys. Acta* 489:390-396, 1977; Bardon et al., *Cancer Lett.* 99:51-58, 1996; and Sprecher and Lee, *Biochim. Biophys. Acta.* 388:113-125, 1975), although some 20:3 is metabolized directly to series 1 eicosanoid metabolic regulators (Hwang, *Fatty Acids in Foods and Their Health Implications*, pp. 545-557, 1992).

It is interesting to note that the alternate pathway of $\Delta^8$-desaturation begins with an elongation step. This elongation is the standard pathway in *Euglena*, which produces substantial amounts of 20:2 (7.4%) and 20:3 (1.4%) (FIG. 2). In mammalian tissue with little or no $\Delta^6$ activity (Grammatikos et al., *Br. J. Cancer* 70:219-227, 1994), this would be the first step by which the essential fatty acids 18:2 and 18:3 are metabolized to their 20-carbon derivatives. Recently there has been a new emphasis on fatty acid chain elongation acting as a regulatory step in fatty acid biosynthesis (Garcia et al., *Lipids* 25:211-215, 1990; Sprecher et al., *Prostag. Leukot. Essent. Fatty Acids* 52:99-101, 1995). Evidence that breast cancer cells may selectively elongate 18:3 in preference to 18:2, and that $\Delta^8$-desaturation follows this elongation (Bardon et al., *Cancer Lett.* 99:51-58, 1996) implies that $\Delta^8$-desaturation may play an important role in some cancer cells.

The identification and cloning of a $\Delta^8$-desaturase gene permit examinations of the alternate pathway for biosynthesis of 20-carbon polyunsaturated fatty acids and will give insight into the possible mechanisms of $\Delta^8$-desaturation. In mammals, operation of this alternative pathway may be confined to specialized tissues, where the demand for polyunsaturated fatty exceeds the supply provided through rate-limiting $\Delta^6$ desaturation. The pathway may be of greater significance where $\Delta^6$ desaturation is reduced or absent. Since fatty acid desaturase metabolism is perturbed in many cell lines, both transformed (Grammatikos et al., *Ann. N. Y. Acad. Sci.* 745:92-105, 1994) and untransformed (Rosenthal, *Prog. Lipid Res.* 26:87-124, 1987), it may be that $\Delta^8$ activity is only revealed in the absence of $\Delta^6$ activity. Alternatively, $\Delta^8$ activity may arise or increase with cell neoplasia. The isolation and examination of this $\Delta^8$ gene, and analysis of its substrate specificity, should facilitate the determination of the role of $\Delta^8$ activity in both normal and cancerous mammalian tissue.

Example 14: Discussion of the *C. elegans* $\Delta^5$-Desaturase

In this example, we describe a region of the *C. elegans* genome located at position 4.88 of chromosome IV is described that contains the $\Delta^5$- and $\Delta^6$-desaturase genes. The amino acid sequences encoded by the two genes are 46% identical to each other, and each contains an N-terminal heme binding domain typical of the electron carrier cytochrome $b_5$ and three histidine boxes. Both genes contain the consensus sequence of the third His box (QXXHH; SEQ. ID NO. 13) that has so far been shown to be unique to the microsomal desaturases involved in double-bond insertion at carbons below position 9.

Despite these similarities, these two microsomal desaturases show absolutely non-overlapping substrate specificities. When overexpressed in the yeast *Saccharomyces cerevisiae*, the *C. elegans* $\Delta^6$-desaturase (FAT-3) specifically acts on two 18-carbon substrates, linoleic and γ-linolenic acid, and always desaturates in a methylene-interrupted pattern (one double bond every three carbons). The mammalian $\Delta^6$-desaturase system has likewise been demonstrated to insert double bonds strictly in a methylene-interrupted pattern and to have no activity on 20-carbon substrates (Schmitz et al., *Lipids* 12:307-313, 1997). The *C. elegans* $\Delta^5$-desaturase (FAT-4), in contrast, acts on a number of 20-carbon substrates, as well as on an endogenous 18:1 fatty acid of yeast, and is capable of inserting double bonds in a non-methylene interrupted pattern.

Non-methylene-interrupted fatty acids such as $20:2\Delta^{5,11}$, $20:3\Delta^{5,11,14}$, $18:2\ \Delta^{5,11}$ have been detected in mammalian cells by feeding $^{14}$C-labeled substrates to rats raised on a fat-deficient diet (Ulman et al., *Biochem. Biophys. Acta* 248:186-197, 1971). However, these fatty acids are considered to be "dead end" metabolites, as they have not been demonstrated to serve as precursors to signaling molecules such as prostaglandins, nor are they detectable in tissue lipids of rats who are not preconditioned on a fat-deficient diet. (We also did not detect these fatty acids in *C. elegans* lipid extracts.)

In yeast expressing the *C. elegans* $\Delta^5$-desaturase gene, the amount of substrate converted was greatest for the metabolically significant substrate $20:3\Delta^{8,11,14}$ (FIG. 13). The amount of $20:2\Delta^{11,14}$ and $20:3\Delta^{11,14,17}$ that was desaturated less than half the amount of conventional substrate that was desaturated. This was consistent with the rates of desaturation in microsomal extracts of mammalian liver, where the rate of conversion of labeled $20:2\Delta^{11,14}$ to $20:3\Delta^{5,11,14}$ is 41% of the rate of conversion of labeled $20:3\Delta^{8,11,14}$ to $20:4\Delta^{5,8,11,14}$ (Bernet et al., *Biochem. Biophys. Acta* 398: 354-313, 1975).

The *C. elegans* fat-3 and fat-4 genes are present in a gene cluster in the same 5' to 3' orientation. Yet, unlike other gene clusters of this sort in *C. elegans*, the downstream fat-3 gene is not transpliced to SL2, and therefore is unlikely to be co-transcribed with the upstream fat-4 gene. The two genes could be located next to each other as a result of an ancient gene-duplication event. The DNA sequences share 54% identity over the entire cDNA coding sequence; however the genes do not share any common intron/exon boundaries (FIG. 8).

This is the first disclosed sequence of a $\Delta^5$-desaturase gene from an animal. The sequence of the *C. elegans*$^5$-desaturase is quite distant from the bacterial and fungal $\Delta^5$-desaturases that have been reported, and this animal sequence should facilitate the search for desaturase-encoding sequences from humans and other mammals. Both the $\Delta^5$- and $\Delta^6$-desaturases are important regulatory enzymes in humans. They participate in critical steps in the pathway to produce precursors for synthesis of hormone-like eicosanoid molecules from the essential dietary fatty acids, linoleic acid and α-linolenic acid. The activities of these desaturases have been shown to be under hormonal and nutritional control, but the mechanism of this control is still unknown.

Certain diseases, such as diabetes, result in low $\Delta^5$-desaturase activity, while HTC cells, isolated from an ascites tumor derived from a solid hepatoma, show increased $\Delta^5$-desaturase activity. The availability of mutational and reverse genetic tools and the expanding knowledge of cellular and developmental biology in *C. elegans* make this an attractive system to study the roles of polyunsaturated fatty acids and their metabolic products in development, reproduction, and other cellular processes of animals.

Example 15: A Plant Cell Transformed with the $\Delta^5$ and $\Delta^8$-Desaturase Genes of the Invention Using the methods described herein, $\Delta^5$- and $\Delta^8$-desaturases of the invention may be cloned and expressed in plants to produce plants with enhanced amounts of 20-carbon polyunsaturated fatty acids. Such plants provide an inexpensive and convenient source of these important fatty acids in a readily harvestable and edible form.

For instance, the $\Delta^5$- and $\Delta^8$-desaturases of the invention can be cloned into a common food crop, such as corn, wheat, potato, tomato, yams, apples, pears, or into oil-seed plants such as sunflower, rapeseed, soy, or peanut plants. The resulting plant would express the appropriate enzyme that would catalyze the formation of 20-carbon polyunsaturated fatty acids. In the case of an oil-seed plant, the seed oil would be a rich source of 20-carbon polyunsaturated fatty acids.

The $\Delta^5$- and $\Delta^8$-desaturase genes may be cloned and expressed either individually, or together in a host plant cell. The corresponding desaturases can be expressed using a variety of different control sequences, such as promoters, enhancers, and 3'-termination sequences. These control sequences can be used to control the expression of each desaturase individually. For example, the $\Delta^5$-desaturase can be cloned such that it is under the control of a strong promoter, and the $\Delta^8$-desaturase can be cloned such that it is under the control of a weak promoter, thus yielding a transgenic plant that expresses more $\Delta^5$-desaturase than $\Delta^8$-desaturase. Furthermore, expression can be controlled by operably linking one or more of the desaturase genes of interest to a promoter that is activated by exposure of the plant cell to an appropriate regulatory agent such as an inducer, repressor, de-repressor or inhibitor agent. Such regulation is discussed above. Alternatively, expression of non-contiguous genes may be coordinated by linking the expression of a first gene with the expression of an inducer or de-repressor molecule that induces or de-represses the expression of a second gene.

The genes of the invention can be integrated into the genome of a plant (for example, by *Agrobacterium*-mediated T-DNA transfer) or animal (for example, by use of broad host-range retroviruses, e.g., an adenovirus vector) so that the $\Delta^5$ and $\Delta^8$-desaturases of the invention are expressed as part of the genome. For transgenic plants, the T-DNA vector may be used that would result in integration of transgenes ($\Delta^5$ and/or $\Delta^8$) into the host cell genome.

For example, the expression of the $\Delta^5$- and $\Delta^8$-desaturases in a plant, such as *Arabidopsis*, can be achieved by constructing a plant transformation vector to introduce the cDNA of each desaturase into the plant. The vector can contain a tissue specific promoter so that the desaturase protein will be expressed during seed development. Examples of seed specific promoters include that for phaseolin (van der Geest and Hall, *Plant Mol. Biol.* 32:579-88, 1996) or the promoter for napin (Stalberg et al., *Plant Mol. Biol.* 23: 671-83, 1993). Other seed-specific promoters that can be used are those located on the genomic BAC clone T24A18 (LOCUS ATT24A18. (1999) 45980 bp *Arabidopsis thaliana* DNA chromosome 4, ACCESSION # AL035680, NID g4490701) of the *Arabidopsis* genome. These promoters regulate seed storage protein expression in *Arabidopsis*. Other promoters which express genes specifically in seeds like those described in (Parcy et al., *Plant Cell* 6:1567-1582, 1994) can also be used. The constructs containing the desaturase coding sequence and promoter sequence can then transferred to standard plant transformation T-DNA vectors similar to pART27 (Gleave, *Plant Mol. Biol.* 20:1203-1207, 1992), pGPTV (Becker et al., *Plant Mol. Biol.* 20:1195-7, 1992), or pJIT119 (Guerineau et al., *Plant Mol. Biol.* 15:127-136, 1992). If the plant is to be transformed with two constructs, i.e. one encoding the $\Delta^8$-desaturase and the other encoding the $\Delta^5$-desaturase, then it is preferable to choose two different selectable markers so that only double transformants will regenerate. For example, the vector carrying the $\Delta^5$-desaturase can be constructed such that it contains the kanamycin (nptII) gene, and the vector carrying the $\Delta^8$-desaturase can be constructed such that it contains the phosphinothricin (bar) gene. Transformants are then selected on media containing kanamycin and phosphinothricin. Transformation of *Arabidopsis* is readily achieved using the *Agrobacterium*-mediated vacuum infiltration process (Katavic et al., *Mol. Gen. Genet.* 245:363-70, 1994) or the floral dip modification of it (Clough and Bent, *Plant J.* 16:735-43, 1998), although several other methods are also commonly used. Transgenic progeny will be identified by selection using the appropriate antibiotic or herbicide, either kanamycin or phosphinothricin, or both. Since the $\Delta^8$ and $\Delta^5$ constructs use different selectable markers the double transformants are readily isolated. Plants which survive the transgenic selection are grown to maturity and their seed harvested. The seeds of transformed plants are analyzed by isolation of fatty acid methyl esters followed by gas chromatography to determine the fatty acid composition.

Plants expressing only the $\Delta^8$-desaturase will desaturate the $20:1\Delta^{11}$ fatty acid that occurs naturally in the *Arabidopsis* seed to $20:2\Delta^{8,11}$. Seed harvested from plants doubly transformed with both desaturases will, in addition, convert the 20:Δ$^{8,11}$ product of the Δ$^8$-desaturase plants to 20:3Δ$^{5,8,11}$ as a result of the expression of the Δ$^5$-desaturase. These changes will be easily detected by the fatty acid methyl ester analysis.

Example 16: a Yeast Cell Transformed with the Δ$^5$- and Δ$^8$-Desaturase Genes of the Invention The cDNA portion of pJW541 (Wallis and Browse, *Arch. Biochem. Biophys.* 365:307-316, 1999) containing the *Euglena* Δ$^8$-desaturase was excised from that plasmid with the restriction enzymes EcoRI and SpeI. The purified DNA fragment representing the insert was ligated into the yeast expression vector pYX232 (R&D Systems, Inc.) that had been prepared by digestion with EcoRI and NheI, to give compatible sticky ends. (Plasmid pYX232 carries the marker conferring yeast prototrophy for tryptophan (TRP1 mutation), and uses the triose phosphate isomerase (TPI) promoter for constitutive expression of the inserted DNA.) The resulting plasmid, pYX232-541, was introduced into the *Saccharomyces cerevisiae* strain already harboring the Δ$^5$-desaturase (pYFAT4; Watts and Browse, *Arch. Biochem. Biophys.* 362:175-182, 1999) plasmid that confers yeast prototrophy for uracil using a lithium acetate transformation procedure (Invitrogen). Transformants were selected simultaneously for uracil and tryptophan prototrophy. Selected colonies arising after the transformation were inoculated into yeast minimal medium that also lacked both uracil and tryptophan.

For analysis of activity, separate cultures were supplemented with one of three fatty acid substrates provided as sodium salts as described (Wallis and Browse, *Arch. Biochem. Biophys.* 365:307-316, 1999). After overnight culture at 28° C., the cultures were harvested by centrifugation and washed. Fatty acid methyl esters were prepared using the standard methods described in Miguel and Browse *J. Biol. Chem.* 267:1502-1509, 1992.

Analysis by gas chromatography indicated that each substrate had been desaturated twice. The incorporation of the three substrates varied, with more unsaturated substrates becoming a greater part of the fatty acid composition of the cells, as seen in other experiments (Wallis and Browse, *Arch. Biochem. Biophys.* 365:307-316, 1999, and Watts and Browse, *Arch. Biochem. Biophys.* 362:175-182, 1999. For the tri-unsaturated substrate 20:3Δ$^{11,14,17}$ the 20-carbon fatty acid represented 37% of the total cellular fatty acid, for 20:2Δ$^{11,14}$ the 20-carbon fatty acid level 21%, and for 20:1Δ$^{11}$ the 20-carbon fatty acid level reached only 13%. However, the activities of the desaturases were substantially identical against all three substrates. Between 70 and 72% of the substrate was not converted, and 17 or 18% underwent a single desaturation by only one of the enzymes. However, for each substrate, between 11 and 13% of the substrate was desaturated by both enzymes acting in concert to produce a fatty acid with two double bonds more than in molecules of the supplied substrate.

TABLE 2

| Fatty acid supplement | Fatty acid uptake* | Unconverted substrate # | One added desaturation # | Doubly desaturated product # |
|---|---|---|---|---|
| 20:3 (11, 14, 17) | 37 | 71 | 17 | 11 20:5 (5, 8, 11, 14, 17) |
| 20:2 (11, 14) | 21 | 70 | 18 | 13 20:4 (5, 8, 11, 14) |
| 20:1 (11) | 13 | 72 | 18 | 11 20:3 (5, 8, 11) |

*as mass percent of whole cell fatty acids as mass percent of incorporated 20-carbon fatty acids

The foregoing embodiments and examples are provided only as examples and are in no way meant to limit the scope of the claimed invention.

It should be apparent to one skilled in the art that the invention described herein can be modified in arrangement and detail without departing from the scope or spirit of the invention. We claim all such modifications.

The references and publications referred to herein are hereby incorporated by reference.

We claim:

1. A transformed plant, bacterial, insect, fungal, or mammalian cell expressing a non-naturally occurring recombinant polypeptide that comprises all of:
   i) a cytochrome b5-like domain;
   ii) three His-box motifs; and
   iii) at least three hydrophobic regions spanning a membrane layer twice;
wherein the polypeptide has an amino acid sequence having at least 50% sequence identity to SEQ ID NO: 2.

2. The transformed plant, bacterial, insect, fungal, or mammalian cell of claim 1, wherein the polypeptide comprises an amino acid sequence at least 70% identical to SEQ ID NO: 2.

3. The transformed plant, bacterial, insect, fungal, or mammalian cell of claim 2, wherein the polypeptide comprises an amino acid sequence at least 80% identical to SEQ ID NO: 2.

4. The transformed plant, bacterial, insect, fungal, or mammalian cell of claim 3, wherein the polypeptide comprises an amino acid sequence at least 90% identical to SEQ ID NO: 2.

5. The transformed plant, bacterial, insect, fungal, or mammalian cell of claim 1, wherein the polypeptide is encoded by a nucleic acid molecule comprising the nucleic acid sequence of SEQ ID NO: 1 or a nucleic acid molecule comprising at least 60% identity to SEQ ID NO: 1.

6. The transformed plant, bacterial, insect, fungal, or mammalian cell of claim 5, wherein the polypeptide is encoded by a nucleic acid molecule comprising at least 70% identity to SEQ ID NO: 1.

7. The transformed plant, bacterial, insect, fungal, or mammalian cell of claim 6, wherein the polypeptide is encoded by a nucleic acid molecule comprising at least 95% identity to SEQ ID NO: 1.

8. The transformed cell of claim 1, wherein the cell is a plant cell of a tomato, potato, yam, apple, pear, rapeseed, sunflower, peanut, soy, wheat, rice, barley, or corn plant.

9. A non-human transgenic organism, comprising the transformed cell of claim 1, wherein the non-human transgenic organism is selected from the group consisting of plants, bacteria, insects, fungi, and mammals.

10. A method for creating a double bond between two carbons in a fatty acid, comprising:
    contacting a fatty acid with at least one transformed plant, bacterial, insect, fungal, or mammalian cell of claim 1; and
    allowing the recombinant desaturase protein expressed therein to create a double-bond between two carbons.

11. The method of claim 10, wherein the transformed plant, bacterial, insect, fungal, or mammalian cell is a transgenic plant, bacterial, insect, fungal, or mammalian organism and the double-bond formation occurs in vivo.

12. The method of claim 10, wherein the desaturase is expressed in vitro and the double-bond formation occurs in vitro.

13. The method of claim 10, further comprising expressing a second desaturase in the transformed plant, bacterial, insect, fungal, or mammalian cell.

14. The method of claim 13, wherein the second desaturase has an amino acid sequence selected from the group consisting of:
    (a) the amino acid sequence as shown in SEQ ID NO: 4;
    (b) an amino acid sequence that differs from that specified in (a) by one or more conservative amino acid substitutions; and
    (c) an amino acid sequences having at least 60% sequence identity to the sequences specified in (a) or (b).

15. The method of claim 11, wherein the transformed plant cell is a transgenic plant and further comprising isolating fatty acid methyl esters from seeds of the transgenic plant.

* * * * *